(12) United States Patent
Furlotti et al.

(10) Patent No.: US 11,472,795 B2
(45) Date of Patent: Oct. 18, 2022

(54) 1H-INDAZOLE-3-CARBOXAMIDE COMPOUNDS AS GLYCOGEN SYNTHASE KINASE 3 BETA INHIBITORS

(71) Applicant: AZIENDE CHIMICHE RIUNITE ANGELINI FRANCESCO—A.C.R.A.F. S.p.A., Rome (IT)

(72) Inventors: Guido Furlotti, Rome (IT); Claudia Cavarischia, Rome (IT); Rosa Buonfiglio, Bologna (IT); Rosella Ombrato, Rome (IT); Tommaso Iacoangeli, Rome (IT)

(73) Assignee: AZIENDE CHIMICHE RIUNITE ANGELINI FRANCESCO—A.C.R.A.F. S.p.A., Rome (IT)

( * ) Notice: Subject to any disclaimer, the term of this patent is extended or adjusted under 35 U.S.C. 154(b) by 91 days.

(21) Appl. No.: 17/051,352

(22) PCT Filed: May 6, 2019

(86) PCT No.: PCT/EP2019/061532
§ 371 (c)(1),
(2) Date: Oct. 28, 2020

(87) PCT Pub. No.: WO2019/215075
PCT Pub. Date: Nov. 14, 2019

(65) Prior Publication Data
US 2021/0053956 A1 Feb. 25, 2021

(30) Foreign Application Priority Data
May 7, 2018 (EP) ..................... 18171084

(51) Int. Cl.
*C07D 409/14* (2006.01)
*C07D 405/12* (2006.01)
*C07D 405/14* (2006.01)

(52) U.S. Cl.
CPC ......... *C07D 409/14* (2013.01); *C07D 405/12* (2013.01); *C07D 405/14* (2013.01)

(58) Field of Classification Search
CPC ... C07D 409/14; C07D 405/12; C07D 405/14
See application file for complete search history.

(56) References Cited

U.S. PATENT DOCUMENTS

| 2014/0378455 | A1 | 12/2014 | Alisi et al. |
| 2015/0057294 | A1 | 2/2015 | Alisi et al. |
| 2015/0266825 | A1* | 9/2015 | Hood ...................... A61P 25/00 548/362.5 |
| 2016/0045485 | A1 | 2/2016 | Alisi et al. |
| 2017/0157121 | A1 | 6/2017 | Alisi et al. |
| 2017/0174657 | A1 | 6/2017 | Alisi et al. |
| 2018/0127377 | A1 | 5/2018 | Hood et al. |

FOREIGN PATENT DOCUMENTS

| WO | WO 2013/124158 A1 | 8/2013 |
| WO | WO 2013/124169 A1 | 8/2013 |
| WO | WO 2015/143380 A1 | 9/2015 |

OTHER PUBLICATIONS

International Search Report and Written Opinion dated Jun. 26, 2019 in PCT/EP2019/061532 filed May 6, 2019.

* cited by examiner

*Primary Examiner* — Matthew P Coughlin
(74) *Attorney, Agent, or Firm* — Oblon, McClelland, Maier & Neustadt, L.L.P.

(57) ABSTRACT

The present invention relates to the 1H-indazole-3-carboxamide compounds as glycogen synthase kinase 3 beta (GSK-3β) inhibitors and to their use in the treatment of GSK-3β-related disorders such as, for example, (i) insulin-resistance disorders; (ii) neurodegenerative diseases; (iii) mood disorders; (iv) schizophrenic disorders; (v) cancerous disorders; (vi) inflammation, (vii) osteoporosis, (viii) cardiac hypertrophy, (ix) epilepsies and (x) neuropathic pain.

20 Claims, No Drawings

1H-INDAZOLE-3-CARBOXAMIDE COMPOUNDS AS GLYCOGEN SYNTHASE KINASE 3 BETA INHIBITORS

CROSS REFERENCE TO RELATED APPLICATIONS

This application is a 371 of International Patent Application No. PCT/EP2019/061532, filed on May 6, 2019, and claims priority to European Patent Application No. 18171084.9, filed on May 7, 2018, both of which are incorporated herein by reference in their entireties.

FIELD OF THE INVENTION

The present invention relates to 1H-indazole-3-carboxamide compounds acting as glycogen synthase kinase 3 beta (GSK-3β) inhibitors and to their use in the treatment of GSK-3β-related disorders such as (i) insulin-resistance disorders; (ii) neurodegenerative diseases; (iii) mood disorders; (iv) schizophrenic disorders; (v) cancerous disorders; (vi) inflammation, (vii) osteoporosis, (viii) cardiac hypertrophy, (ix) epilepsies and (x) neuropathic pain.

STATE OF THE ART

Protein kinases constitute a large family of structurally related enzymes, which transfer phosphate groups from high-energy donor molecules (such as adenosine triphosphate, ATP) to specific substrates, usually proteins. After phosphorylation, the substrate undergoes to a functional change, by which kinases can modulate various biological functions.

In general, protein kinases can be divided in several groups, according to the substrate that is phosphorylated. For example, serine/threonine kinase phosphorylates the hydroxyl group on the side chain of serine or threonine aminoacid.

Glycogen synthase kinases 3 (GSK-3) are constitutively active multi-functional enzymes, quite recently discovered, belonging to the serine/threonine kinases group.

Human GSK-3 are encoded by two different and independent genes, which leads to GSK-3α and GSK-3β proteins, with molecular weights of about 51 and 47 kDa, respectively. The two isoforms share nearly identical sequences in their kinase domains, while outside of the kinase domain, their sequences differ substantially (Benedetti et al., *Neuroscience Letters*, 2004, 368, 123-126). GSK-3α is a multifunctional protein serine kinase and GSK-3D is a serine-threonine kinase.

It has been found that GSK-3β is widely expressed in all tissues, with widespread expression in the adult brain, suggesting a fundamental role in neuronal signaling pathways (Grimes and Jope, *Progress in Neurobiology*, 2001, 65, 391-426). Interest in glycogen synthase kinases 3 arises from its role in various physiological pathways, such as, for example, metabolism, cell cycle, gene expression, embryonic development oncogenesis and neuroprotection (Geetha et al., *British Journal Pharmacology*, 2009, 156, 885-898).

GSK-3β was originally identified for its role in the regulation of glycogen synthase for the conversion of glucose to glycogen (Embi et al., *Eur J Biochem*, 1980, 107, 519-527). GSK-3β showed a high degree of specificity for glycogen synthase.

Type 2 diabetes was the first disease condition implicated with GSK-3β, due to its negative regulation of several aspects of insulin signaling pathway. In this pathway 3-phosphoinositide-dependent protein kinase 1 (PDK-1) activates PKB, which in turn inactivates GSK-3β. This inactivation of GSK-3β leads to the dephosphorylation and activation of glycogen synthase, which helps glycogen synthesis (Cohen et al., *FEBS Lett.*, 1997, 410, 3-10). Moreover, selective inhibitors of GSK-3β are expected to enhances insulin signaling in prediabetic insulin-resistant rat skeletal muscle, thus making GSK-3β an attractive target for the treatment of skeletal muscle insulin resistance in the pre-diabetic state (Dokken et al., *Am J. Physiol. Endocrinol. Metab.*, 2005, 288, E1188-E1194).

GSK-3β was also found to be a potential drug target in others pathological conditions due to insulin-resistance disorders, such as syndrome X, obesity and polycystic ovary syndrome (Ring D B et al., *Diabetes*, 2003, 52: 588-595).

It has been found that GSK-3β is involved in the abnormal phosphorylation of pathological tau in Alzheimer's disease (Hanger et al., *Neurosci. Lett.*, 1992, 147, 58-62; Mazanetz and Fischer, *Nat Rev Drug Discov.*, 2007, 6, 464-479; Hong and Lee, *J. Biol. Chem.*, 1997, 272, 19547-19553). Moreover, it was proved that early activation of GSK-3β, induced by apolipoprotein ApoE4 and β-amyloid, could lead to apoptosis and tau hyperphosphorylation (Cedazo-Minguez et al., *Journal of Neurochemistry*, 2003, 87, 1152-1164). Among other aspect of Alzheimer's disease, it was also reported the relevance of activation of GSK-3β at molecular level (Hernandez and Avila, *FEBS Letters*, 2008, 582, 3848-3854).

Moreover, it was demonstrated that GSK-3β is involved in the genesis and maintenance of neurodegenerative changes associated with Parkinson's disease (Duka T. et al., *The FASEB Journal*, 2009; 23, 2820-2830).

Accordingly to these experimental observations, inhibitors of GSK-3β may find applications in the treatment of the neuropathological consequences and the cognitive and attention deficits associated with tauopathies; Alzheimer's disease; Parkinson's disease; Huntington's disease (the involvement of GSK-3β in such deficits and diseases is disclosed in Meijer L. et al., *TRENDS Pharm Sci*, 2004; 25, 471-480); dementia, such as, but not limited to, vascular dementia, post-traumatic dementia, dementia caused by meningitis and the like; acute stroke; traumatic injuries; cerebrovascular accidents; brain and spinal cord trauma; peripheral neuropathies; retinopathies and glaucoma (the involvement of GSK-3β in such conditions is disclosed in WO 2010/109005).

Furthermore, GSK-3β has been linked to the mood disorders, such as bipolar disorders, depression, and schizophrenia.

Inhibition of GSK-3β may be an important therapeutic target of mood stabilizers, and regulation of GSK-3β may be involved in the therapeutic effects of other drugs used in psychiatry. Dysregulated GSK-3β in mood disorder, bipolar disorder, depression and schizophrenia could have multiple effects that could impair neural plasticity, such as modulation of neuronal architecture, neurogenesis, gene expression and the ability of neurons to respond to stressful, potentially lethal conditions (Jope and Roh, *Curr. Drug Targets*, 2006, 7, 1421-1434).

The role of GSK-3β in mood disorder was highlighted by the study of lithium and valproate (Chen et al., *J. Neurochem.*, 1999, 72, 1327-1330; Klein and Melton, *Proc. Natl. Acad. Sci. USA*, 1996, 93, 8455-8459), both of which are GSK-3β inhibitors and are used to treat mood disorders. There are also existing reports from the genetic perspective supporting the role of GSK-3β in the disease physiology of bipolar disorder (Gould, *Expert. Opin. Ther. Targets*, 2006, 10, 377-392).

It was reported a decrease in AKT1 protein levels and its phosphorylation of GSK-3β at Serine-9 in the peripheral lymphocytes and brains of individuals with schizophrenia. Accordingly, this finding supports the proposal that alterations in AKT1-GSK-3β signaling contribute to schizophrenia pathogenesis (Emamian et al., *Nat Genet*, 2004, 36, 131-137).

Additionally, the role of GSK-3β in cancer is a well-accepted phenomenon.

The potential of small molecules that inhibit GSK-3β has been evidenced for some specific cancer treatments (Jia Luo, *Cancer Letters*, 2009, 273, 194-200). GSK-3β expression and activation are associated with prostate cancer progression (Rinnab et al., *Neoplasia*, 2008, 10, 624-633) and the inhibition of GSK3b was also proposed as specific target for pancreatic cancer (Garcea et al., *Current Cancer Drug Targets*, 2007, 7, 209-215) and ovarian cancer (Qi Cao et al., *Cell Research*, 2006, 16 671-677). Acute inhibition of GSK-3β in colon-rectal cancer cells activates p53-dependent apoptosis and antagonizes tumor growth (Ghosh et al., Clin Cancer Res 2005, 11, 4580-4588).

The identification of a functional role for GSK-3β in MLL-associated leukaemia suggests that GSK-3β inhibition may be a promising therapy that is selective for transformed cells that are dependent on HOX overexpression (Birch et al., *Cancer Cell*, 2010, 17, 529-531).

GSK-3β is involved in numerous inflammatory signalling pathways, for example, among others GSK-3β inhibition has been shown to induce secretion of the anti-inflammatory cytokine IL-10. According to this finding, GSK-3β inhibitors could be useful to regulate suppression of inflammation (G. Klamer et al., *Current Medicinal Chemistry*, 2010, 17(26), 2873-2281, Wang et al., Cytokine, 2010, 53, 130-140).

Recent studies have also identified the role of GSK-3β in some different diseases such as osteoporosis, cardiac hypertrophy, epilepsies and neuropathic pain.

In the former case, inhibition of GSK-3β has been shown to increase bone mass, as reported by J. Feng et al. in "*Photoactivation of TAZ via Akt/GSK-3β signaling pathway promotes osteogenic differentiation*", *Int J Biochem Cell Biol.* 2015 September; 66:59-68. He revealed a novel mechanism that Akt/GSK3β/TAZ (transcriptional co-activator with PDZ-binding motif) activated by low-power laser irradiation (LPLI) enhances osteoblast differentiation. This technique increases the protein level and nuclear aggregation of TAZ through inhibition of its serine phosphorylation dependent on Akt/GSK-3β signaling.

GSK-3β is a key anti-hypertrophic factor in cardiac cells that regulates both the nuclear residence and the activity of a specific substrate, the nuclear factor of activated T-cells (NFAT). Under hypertrophic stimulation, i.e. by testosterone, GSK-3β is phosphorylated at Ser9, which inhibits its activity, causing the hyper activation of NFAT and the subsequently increasing of cardiac myocyte hypertrophy (Duran J. et al., *GSK-3β/NFAT Signaling Is Involved in Testosterone-Induced Cardiac Myocyte Hypertrophy. PLoS One.* 2016 Dec. 15; 11(12)).

Z. Li et al., in "*Valproate Attenuates Endoplasmic Reticulum Stress-Induced Apoptosis in SH-SY5Y Cells via the AKT/GSK-3β Signaling Pathway*", *Int J Mol Sci.* 2017 Feb. 8; 18(2) underlined the correlation between valproate (VPA) and the AKT and GSK-3β pathways. VPA treatment up-regulated the phosphorylation of AKT and inhibited the expression of GSK-3β. This finding suggests that the neuroprotective effects of VPA are also mediated through the activation of the AKT/GSK-3β signaling pathway.

Finally, M. Rahmati et al., in "*Decreased Activity in Neuropathic Pain Form and Gene Expression of Cyclin-Dependent Kinase5 and Glycogen Synthase Kinase-3 Beta in Soleus Muscle of Wistar Male Rats*", *Iran Red Crescent Med J.* 2015 June; 17(6), showed that increase in GSK-3β in neuropathic pain can further promote pain-related disorders and soleus muscle atrophy.

A review on GSK-3β, its function, its therapeutic potential and its possible inhibitors is given in S. Phukan et al., "*GSK-3β: role in therapeutic landscape and development of modulators*", British Journal of Pharmacology (2010), 160, 1-19 and in E. Beurel et al., "*Glycogen synthase kinase-3 (GSK-3): Regulation, actions, and diseases*", Pharmacology & Therapeutics 148 (2015) 114-131.

WO 2004/014864 discloses 1H-indazole-3-carboxamide compounds as selective cyclin-dependant kinases (CDK) inhibitors. Such compounds are assumed to be useful in the treatment of cancer, through a mechanism mediated by $CDK_2$, and neurodegenerative diseases, in particular Alzheimer's disease, through a mechanism mediated by $CDK_5$, and as anti-viral and anti-fungine, through a mechanism mediated by $CDK_7$, $CDK_8$ and $CDK_9$.

Cyclin-dependant kinases (CDKs) are serine/threonine kinases, first discovered for their role in regulating the cell cycle. CDKs are also involved in regulating transcription, mRNA processing, and the differentiation of nerve cells. Such kinases activate only after their interaction and binding with regulatory subunits, namely cyclins.

WO2015143380A1 and U.S. Pat. No. 9,745,271B2 disclose 1H-indazole-3-carboxamide compounds as active ingredients in the treatment of disorders characterized by the activation of Wnt pathway signaling (e.g., cancer, abnormal cellular proliferation, angiogenesis, Alzheimer's disease, lung disease, fibrotic disorders, cartilage (chondral) defects, and osteoarthritis), the modulation of cellular events mediated by Wnt pathway signaling, and neurological conditions/disorders/diseases linked to overexpression of DYRK1A.

Moreover, 1H-indazole-3-carboxamide compounds were also described as analgesics in the treatment of chronic and neuropathic pain (see, for example, WO 2004/074275 and WO 2004/101548) and as 5-$HT_4$ receptor antagonists, useful in the treatment of gastrointestinal disorders, central nervous system disorders and cardiovascular disorders (see, for example, WO 1994/10174).

Finally, certain 1H-indazole-3-carboxamide compounds acting as glycogen synthase kinase 3 beta (GSK-3β) inhibitors and the use thereof in the treatment of GSK-3β-related disorders such as (i) insulin-resistance disorders; (ii) neurodegenerative diseases; (iii) mood disorders; (iv) schizophrenic disorders; (v) cancerous disorders; and (vi) inflammation have been disclosed in international patent publications WO2013124158 and WO2013124169.

SUMMARY OF THE INVENTION

As GSK-3β had been only recently discovered as a pharmacological target, there is a strong need to find compounds that selectively inhibits GSK-3β.

The Applicant has surprisingly found new 1H-indazole-3-carboxamide compounds according to the following formula (I).

The Applicant has also surprisingly found that said new compounds are capable of inhibit GSK-3β and have very high affinity for GSK-3β, when compared with other kinases, and increased selectivity with respect to the hERG channel.

Thus, said compounds are capable of selectively inhibiting GSK-3β without interactions with the hERG ion channel which may be responsible for adverse side effects in the cardiovascular system.

Accordingly, the compounds according to this invention are useful for the treatment of the pathological conditions arising from the uncontrolled activation and/or over-expression of GSK-3β, selected from the group comprising (i) insulin-resistance disorders, such as type-2 diabetes, syndrome X, obesity and polycystic ovary syndrome; (ii) neurodegenerative diseases, such as Parkinson's disease, Alzheimer's disease and Huntington's disease; (iii) mood disorders, such as bipolar disorders and depressive disorders; (iv) schizophrenic disorders; (v) cancerous disorders, such as prostate, pancreatic, ovarian, and colon-rectal cancer and MLL-associated leukaemia; (vi) inflammation, (vii) osteoporosis, (viii) cardiac hypertrophy, (ix) epilepsies and (x) neuropathic pain.

Then, in a first aspect, the present invention relates to 1H-indazole-3-carboxamide compounds having the following general formula (I):

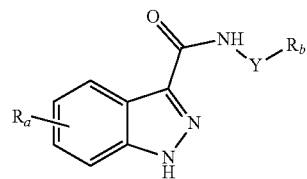

(I)

wherein
$R_a$ is a carbocyclic or heterocyclic ring, aliphatic or aromatic, having from 3 to 12 members, optionally substituted by one or more substituents selected from the group consisting of halogen, hydroxy, $C_1$-$C_6$ alkyl, hydroxy $C_1$-$C_6$ alkyl, $C_1$-$C_6$ alkoxy, hydroxy $C_1$-$C_6$ alkoxy, $C_1$-$C_6$ alkoxy $C_1$-$C_6$ alkyl, $C_1$-$C_6$ alkoxy $C_1$-$C_6$ alkoxy and $C_1$-$C_6$ alkyl amino;

Y is a bond, a $C_1$-$C_6$ alkyl, $C_2$-$C_6$ alkenyl or $C_2$-$C_6$ alkynyl group, optionally substituted by one or more substituents selected from the group consisting of halogen, hydroxy, —$NH_2$, $C_1$-$C_3$ alkyl and $C_1$-$C_3$ alkoxy;

$R_b$ is an aliphatic heterocyclic ring having from 5 to 10 members comprising at least one heteroatom selected from S and O, optionally substituted by one or more substituents selected from the group consisting of halogen, hydroxy, —$NH_2$, oxo (═O), $C_1$-$C_3$ alkyl and $C_1$-$C_3$ alkoxy;

and its salts of addition with pharmaceutically acceptable organic and inorganic acids and bases provided that when $R_b$ is a oxanyl group, Y is not a bond, and when $R_b$ is a oxolanyl group and $R_a$ is a pyridinyl or a monofluoropyridinyl group, Y is not a —$CH_2$— group.

In a second aspect, the present invention relates to a pharmaceutical composition comprising at least one compound of formula (I) as described above and at least one inert pharmaceutically acceptable excipient.

In a third aspect, the present invention relates to the use of 1H-indazole-3-carboxamide compounds having the following general formula (I):

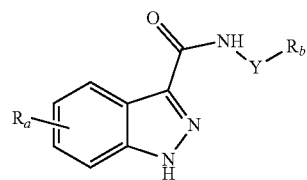

(I)

wherein
$R_a$ is a carbocyclic or heterocyclic ring, aliphatic or aromatic, having from 3 to 12 members, optionally substituted by one or more substituents selected from the group consisting of halogen, hydroxy, $C_1$-$C_6$ alkyl, hydroxy $C_1$-$C_6$ alkyl, $C_1$-$C_6$ alkoxy, hydroxy $C_1$-$C_6$ alkoxy, $C_1$-$C_6$ alkoxy $C_1$-$C_6$ alkyl, $C_1$-$C_6$ alkoxy $C_1$-$C_6$ alkoxy and $C_1$-$C_6$ alkyl amino;

Y is a bond, a $C_1$-$C_6$ alkyl, $C_2$-$C_6$ alkenyl or $C_2$-$C_6$ alkynyl group, optionally substituted by one or more substituents selected from the group consisting of halogen, hydroxy, —$NH_2$, $C_1$-$C_3$ alkyl and $C_1$-$C_3$ alkoxy;

$R_b$ is an aliphatic heterocyclic ring having from 5 to 10 members comprising at least one heteroatom selected from S and O, optionally substituted by one or more substituents selected from the group consisting of halogen, hydroxy, —$NH_2$, oxo (═O), $C_1$-$C_3$ alkyl and $C_1$-$C_3$ alkoxy;

and its salts of addition with pharmaceutically acceptable organic and inorganic acids and bases;

for the treatment of a disease arising from the uncontrolled activation and/or over-expression of GSK-3β, selected from the group consisting of (i) insulin-resistance disorders, such as type-2 diabetes, syndrome X, obesity and polycystic ovary syndrome; (ii) neurodegenerative diseases, such as Parkinson's disease, Alzheimer's disease and Huntington's disease; (iii) mood disorders, such as bipolar disorders and depressive disorders; (iv) schizophrenic disorders; (v) cancerous disorders, such as prostate, pancreatic, ovarian, and colon-rectal cancer and MLL-associated leukaemia; (vi) inflammation, (vii) osteoporosis, (viii) cardiac hypertrophy, (ix) epilepsies and (x) neuropathic pain.

In a fourth aspect, the present invention relates to a method of treatment of a pathological state arising from the uncontrolled activation and/or over-expression of GSK-3β, selected from the group consisting of (i) insulin-resistance disorders, such as type-2 diabetes, syndrome X, obesity and polycystic ovary syndrome; (ii) neurodegenerative diseases, such as Parkinson's disease, Alzheimer's disease and Huntington's disease; (iii) mood disorders, such as bipolar disorders and depressive disorders; (iv) schizophrenic disorders; (v) cancerous disorders, such as prostate, pancreatic, ovarian, and colon-rectal cancer and MLL-associated leukaemia; (vi) inflammation, (vii) osteoporosis, (viii) cardiac hypertrophy, (ix) epilepsies and (x) neuropathic pain by the administration to a human being in need thereof of an effective amount of a 1H-indazole-3-carboxamide having the following general formula (I):

(I)

wherein $R_a$ is a carbocyclic or heterocyclic ring, aliphatic or aromatic, having from 3 to 12 members, optionally substituted by one or more substituents selected from the group consisting of halogen, hydroxy, $C_1$-$C_6$ alkyl, hydroxy $C_1$-$C_6$ alkyl, $C_1$-$C_6$ alkoxy, hydroxy $C_1$-$C_6$ alkoxy, $C_1$-$C_6$ alkoxy $C_1$-$C_6$ alkyl, $C_1$-$C_6$ alkoxy $C_1$-$C_6$ alkoxy and $C_1$-$C_6$ alkyl amino;

Y is a bond, a $C_1$-$C_6$ alkyl, $C_2$-$C_6$ alkenyl or $C_2$-$C_6$ alkynyl group, optionally substituted by one or more substituents selected from the group consisting of halogen, hydroxy, —NH$_2$, $C_1$-$C_3$ alkyl and $C_1$-$C_3$ alkoxy;

$R_b$ is an aliphatic heterocyclic ring having from 5 to 10 members comprising at least one heteroatom selected from S and O, optionally substituted by one or more substituents selected from the group consisting of halogen, hydroxy, —NH$_2$, oxo (=O), $C_1$-$C_3$ alkyl and $C_1$-$C_3$ alkoxy;

and its salts of addition with pharmaceutically acceptable organic and inorganic acids and bases.

The present invention also includes the prodrugs, stereoisomers, and enantiomers of the compounds of formula (I) described above.

DETAILED DESCRIPTION OF THE INVENTION

According to a preferred embodiment of the invention, the meanings of $R_a$, $R_b$ and Y of the formula (I) above are described here in below.

Preferably, $R_a$ is a carbocyclic or heterocyclic ring, aliphatic or aromatic, having from 4 to 10 members, optionally substituted by one or more substituents selected from the group consisting of halogen, hydroxy, $C_1$-$C_6$ alkyl, hydroxy $C_1$-$C_6$ alkyl, $C_1$-$C_6$ alkoxy, hydroxy $C_1$-$C_6$ alkoxy, $C_1$-$C_6$ alkoxy $C_1$-$C_6$ alkyl, $C_1$-$C_6$ alkoxy $C_1$-$C_6$ alkoxy and $C_1$-$C_6$ alkyl amino.

More preferably, $R_a$ is a carbocyclic or heterocyclic ring, aliphatic or aromatic, having from 5 to 6 members, optionally substituted by one or more substituents, selected from the group consisting of halogen, hydroxy, $C_1$-$C_6$ alkyl, hydroxy $C_1$-$C_6$ alkyl, $C_1$-$C_6$ alkoxy, hydroxy $C_1$-$C_6$ alkoxy, $C_1$-$C_6$ alkoxy $C_1$-$C_6$ alkyl, $C_1$-$C_6$ alkoxy $C_1$-$C_6$ alkoxy and $C_1$-$C_6$ alkyl amino.

Particularly, the carbocyclic or etherocyclic ring, aliphatic or aromatic, having from 5 to members can be selected from the group consisting of phenyl, cyclohexane, cyclopentane, pyridine, pyrazine, pyrimidine, pyridazine, piperidine, piperazine, furan, thiophene, pyrrole, pyrrolidine, imidazole, morpholine, thiazole, thiazolidine, thiadiazole, thiadiazolidine, oxazole, oxazolidine, isoxazole, isoxazolidine, and pyrazole.

Even more preferably, $R_a$ is an aromatic carbocyclic or heterocyclic ring, having 6 members, optionally substituted by one or two substituents selected from the group consisting of halogen, hydroxy, $C_1$-$C_6$ alkyl, hydroxy $C_1$-$C_6$ alkyl, $C_1$-$C_6$ alkoxy, hydroxy $C_1$-$C_6$ alkoxy, $C_1$-$C_6$ alkoxy $C_1$-$C_6$ alkyl, $C_1$-$C_6$ alkoxy $C_1$-$C_6$ alkoxy and $C_1$-$C_6$ alkyl amino.

Particularly, the aromatic carbocyclic ring represented by $R_a$ is an aryl group or a naphthyl group. Advantageously, the aromatic carbocyclic ring represented by $R_a$ is a phenyl group.

Particularly, the aromatic heterocyclic ring represented by $R_a$ is a pyridinyl group, a pyrimidinyl group, or a pyrrolyl group. Advantageously, the aromatic heterocyclic ring represented by $R_a$ is a pyridinyl group.

Preferably, Y is a bond or a $C_1$-$C_6$ alkyl group, optionally substituted by one or more substituents selected from the group consisting of halogen, hydroxy, —NH$_2$, $C_1$-$C_3$ alkyl and $C_1$-$C_3$ alkoxy.

More preferably, Y is a $C_1$-$C_6$ alkyl group, optionally substituted by one or more substituents selected from the group consisting of halogen, hydroxy, —NH$_2$, $C_1$-$C_3$ alkyl and $C_1$-$C_3$ alkoxy.

Even more preferably, Y is a $C_1$-$C_3$ alkyl group, optionally substituted by one or more substituents selected from the group consisting of halogen, hydroxy, —NH$_2$, $C_1$-$C_3$ alkyl and $C_1$-$C_3$ alkoxy.

Preferably, $R_b$ is an aliphatic heterocyclic ring having from 5 to 6 members comprising at least one heteroatom selected from S and O, optionally substituted by one or more substituents selected from the group consisting of halogen, hydroxy, —NH$_2$, oxo (=O), $C_1$-$C_3$ alkyl and $C_1$-$C_3$ alkoxy.

More preferably, $R_b$ is an aliphatic heterocyclic ring having from 5 to 6 members comprising at least one oxygen atom, optionally substituted by one or more substituents selected from the group consisting of halogen, hydroxy, —NH$_2$, oxo (=O), $C_1$-$C_3$ alkyl and $C_1$-$C_3$ alkoxy.

Particularly, the aliphatic heterocyclic ring represented by $R_b$ is a thiolanyl group, a oxolanyl group, a thianyl group or a oxanyl group. Advantageously, the aromatic heterocyclic ring represented by $R_b$ is a 1,1-dioxothiolanyl group, a oxolanyl group or a oxanyl group.

In the present description and in the following claims, the term "$C_1$-$C_6$ alkyl" means a linear or branched alkyl chain comprising from 1 to 6 carbon atoms, such as for example methyl, ethyl, propyl, isopropyl, n-butyl, isobutyl, sec-butyl, tert-butyl, n-pentyl, isopentyl, neopentyl, tert-pentyl, sec-pentyl, 3-pentyl, n-hexyl, isohexyl, neo-hexyl, 3-methylpentyl, 2,3-dimethylbutyl.

In the present description and in the following claims, the term "hydroxy $C_1$-$C_6$ alkyl" has the meaning of a "$C_1$-$C_6$ alkyl" group wherein one or more hydrogen atom of the alkyl chain is substituted by a hydroxy group. As an example, the term hydroxy $C_1$ alkyl means the group HO—CH$_2$—.

In the present description and in the following claims, the term "$C_1$-$C_4$ alkyl" means a linear or branched alkyl chain comprising from 1 to 4 carbon atoms, such as for example methyl, ethyl, propyl, isopropyl, n-butyl, isobutyl, sec-butyl, and tert-butyl.

In the present description and in the following claims, the term "$C_1$-$C_3$ alkyl" means a linear or branched alkyl chain comprising from 1 to 3 carbon atoms, such as for example methyl, ethyl, propyl, isopropyl.

In the present description and in the following claims, the term "hydroxy $C_1$-$C_3$ alkyl" has the meaning of a "$C_1$-$C_3$ alkyl" group wherein one or more hydrogen atom of the alkyl chain is substituted by a hydroxyl group.

In the present description and in the following claims, the term "$C_1$-$C_6$ alkoxy" means a linear or branched alkoxy chain comprising from 1 to 6 carbon atoms, such as for example methoxy, ethoxy, propoxy, isopropoxy, n-butoxy, isobutoxy, sec-butoxy, tert-butoxy, n-pentoxy, isopentoxy, neopentoxy, tert-pentoxy, sec-pentoxy, 3-pentoxy, n-hexoxy, isohexoxy, neo-hexoxy, 3-methyl-pentoxy, 2,3-dimethylbutoxy.

In the present description and in the following claims, the term "hydroxy $C_1$-$C_6$ alkoxy" has the meaning of a "$C_1$-$C_6$ alkoxy" group wherein one or more hydrogen atom of the alkyl chain is substituted by a hydroxyl group. As an example, the term hydroxy $C_1$ alkoxy means the group HO—CH$_2$O—.

In the present description and in the following claims, the term "$C_1$-$C_6$ alkoxy $C_1$-$C_6$ alkyl" has the meaning of a "$C_1$-$C_6$ alkyl" group wherein one or more hydrogen atom of the alkyl chain is substituted by a $C_1$-$C_6$ alkoxy group. As an example, the term $C_1$ alkoxy $C_1$ alkyl means the group $CH_3O$—$CH_2$—.

In the present description and in the following claims, the term "$C_1$-$C_6$ alkoxy $C_1$-$C_6$ alkoxy" has the meaning of a "$C_1$-$C_6$ alkoxy" group wherein one or more hydrogen atom of the alkyl chain is substituted by a further $C_1$-$C_6$ alkoxy group. As an example, the term $C_1$ alkoxy $C_1$ alkoxy means the group $CH_3O$—$CH_2O$—.

In the present description and in the following claims, the term "$C_1$-$C_3$ alkoxy" means a linear or branched alkoxy chain comprising from 1 to 3 carbon atoms, such as for example methoxy, ethoxy, propoxy, isopropoxy.

In the present description and in the following claims, the term "hydroxy $C_1$-$C_3$ alkoxy" has the meaning of a "$C_1$-$C_3$ alkoxy" group wherein one or more hydrogen atom of the alkyl chain is substituted by a hydroxyl group.

In the present description and in the following claims, the term "$C_2$-$C_6$ alkenyl" means a divalent linear or branched alkylene chain comprising from 2 to 6 carbon atoms, such as for example ethenyl (—CH=CH—), propenyl (—CH=CH—$CH_2$— or —C($CH_3$)=CH—) or butenyl (—CH=CH— $CH_2CH_2$— or —$CH_2$CH=CH—$CH_2$— or —C($CH_3$)=CH—$CH_2$—), pentenyl (—C=C— $CH_2CH_2CH_2$— or —$CH_2CH_2$—C=C—$CH_2$— or —C($CH_2CH_3$)—C=C—), or hexenyl (—C=C— $CH_2CH_2CH_2CH_2$— or —$CH_2CH_2$C=C—$CH_2CH_2$— or —$CH_2CH_2$C($CH_3$)—C=C—).

In the present description and in the following claims, the term "$C_2$-$C_4$ alkenyl" means a divalent linear or branched alkylen chain comprising from 2 to 6 carbon atoms, such as for example ethenyl (—CH=CH—), propenyl (—CH=CH—$CH_2$— or —C($CH_3$)=CH—) or butenyl (—CH=CH— $CH_2CH_2$— or —$CH_2$CH=CH—$CH_2$— or —C($CH_3$)=CH—$CH_2$—).

In the present description and in the following claims, the term "$C_2$-$C_6$ alkynyl means a divalent linear or branched alkynyl chain comprising from 2 to 6 carbon atoms, such as for example ethynyl (—C≡C—), propynyl (—C≡C—$CH_2$— or —$CH_2$—C≡C—), butynyl (—C≡C—$CH_2CH_2$— or —$CH_2$—C≡C—$CH_2$— or —C($CH_3$)—C≡C—), pentynyl (—C≡C—$CH_2CH_2CH_2$— or —$CH_2CH_2$—C≡C—$CH_2$— or —C($CH_2CH_3$)—C≡C—), or hexynyl (—C≡C— $CH_2CH_2CH_2CH_2$— or —$CH_2CH_2$C≡C—$CH_2CH_2$— or —$CH_2CH_2$C($CH_3$)—C≡C—).

In the present description and in the following claims, the term "$C_2$-$C_4$ alkynyl means a divalent linear or branched alkynyl chain comprising from 2 to 4 carbon atoms, such as for example ethynyl (—C≡C—), propynyl (—C≡C—$CH_2$— or —$CH_2$—C≡C—), butynyl (—C≡C—$CH_2CH_2$— or —$CH_2$—C≡C—$CH_2$— or —C($CH_3$)—C≡C—).

In the present description and in the following claims, the term "$C_1$-$C_6$ alkyl amino" has the meaning of a "$C_1$-$C_6$ alkyl" group wherein one or more hydrogen atoms are substituted by an amino group having the formula —$NR_1R_2$, wherein $R_1$ and $R_2$ are independently a hydrogen atom, a $C_1$-$C_4$ alkyl group, a $C_2$-$C_4$ alkenyl group, a $C_2$-$C_4$ alkynyl group, and a phenyl group, or $R_1$ and $R_2$ together with the nitrogen atom form an aliphatic heterocyclic ring having 5 to 6 members, optionally comprising at least one additional heteroatom selected from N, S and O.

Preferably, the aliphatic heterocyclic ring formed by $R_1$ and $R_2$ together with the nitrogen atom of the —$NR_1R_2$ amino group is a pyrrolidine, oxazolidine, thiazolidine, piperidine, piperazine, morpholine, or thiomorpholine ring. Advantageously, the aliphatic heterocyclic ring formed by $R_1$ and $R_2$ together with the nitrogen atom of the —$NR_1R_2$ amino group is a pyrrolidine, piperidine or morpholine ring.

Certain compounds of this invention may exist in tautomeric forms, and this invention includes all such tautomeric forms of those compounds unless otherwise specified.

Unless otherwise stated, structures depicted herein are also meant to include all stereochemical forms of the structure; i.e., the R and S configurations for each asymmetric center. Thus, single stereochemical isomers as well as enantiomeric and diastereomeric mixtures of the present compounds are within the scope of the invention. Thus, this invention encompasses each diastereomer or enantiomer substantially free of other isomers (>90%, and preferably >95%, free from other stereoisomers on a molar basis) as well as a mixture of such isomers.

Particular optical isomers can be obtained by resolution of the racemic mixtures according to conventional processes, e.g., by formation of diastereomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereomers by crystallization followed by liberation of the optically active bases from these salts. A different process for separation of optical isomers involves the use of a chiral chromatography column optimally chosen to maximize the separation of the enantiomers. Still another method involves synthesis of covalent diastereomers by reacting compounds of the invention with an optically pure acid in an activated form or an optically pure isocyanate. The synthesized diastereomers can be separated by conventional means such as chromatography, distillation, crystallization or sublimation, and then hydrolysed to deliver the enantiomerically pure compound. Optically active compounds of the invention can be obtained by using active starting materials. These isomers may be in the form of a free acid, a free base, an ester or a salt.

The compounds of this invention can exist in radiolabeled form, i.e., said compounds may contain one or more atoms containing an atomic mass or mass number different from the atomic mass or mass number ordinarily found in nature. Radioisotopes of hydrogen, carbon, phosphorous, fluorine and chlorine include $^3H$, $^{14}C$, $^{32}P$, $^{35}S$, $^{18}F$ and $^{36}Cl$, respectively. Compounds of this invention which contain those radioisotopes and/or other radioisotopes of other atoms are within the scope of this invention. Tritiated, i.e., $^3H$, and carbon-14, i.e., $^{14}C$, radioisotopes are particularly preferred for their ease of preparation and detectability.

Radiolabeled compounds of this invention can generally be prepared by methods well known to those skilled in the art. Conveniently, such radiolabeled compounds can be prepared by carrying out the procedures disclosed herein except substituting a readily available radiolabeled reagent for a non-radiolabelled reagent.

The compounds according to the present invention are preferably employed as salts with pharmaceutically acceptable organic and inorganic acids or bases.

Preferably, the pharmaceutically acceptable organic acids are selected from the group consisting of oxalic, maleic, methanesulphonic, paratoluenesulphonic, succinic, citric, malic, tartaric lactic acid.

Preferably, the pharmaceutically acceptable organic bases are selected from the group consisting of tromethamine, lysine, arginine, glycine, alanine and ethanolamine.

Preferably, the pharmaceutically acceptable inorganic acids are selected from the group consisting of hydrochloric, hydrobromic, phosphoric and sulphuric acid.

Preferably, the pharmaceutically acceptable inorganic bases are selected from the group consisting of hydroxide or carbonate of alkaline or alkaline-earth metals, such as sodium, potassium and calcium.

The present invention also includes the prodrugs, stereoisomers, and enantiomers of the compounds of formula (I) described above.

As used herein the term "prodrug" refers to an agent, which is converted into the parent drug in vivo by some physiological chemical process (e.g., a prodrug on being brought to the physiological pH is converted to the desired drug form). Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present invention wherein it is administered as an ester (the "prodrug") to facilitate transmittal across a cell membrane where water solubility is not beneficial, but then it is metabolically hydrolyzed once inside the cell where water solubility is beneficial.

Prodrugs have many useful properties. For example, a prodrug may be more water-soluble than the ultimate drug, thereby facilitating intravenous administration of the drug. A prodrug may also have a higher level of oral bioavailability than the ultimate drug. After administration, the prodrug is enzymatically or chemically cleaved to deliver the ultimate drug in the blood or tissue.

Ester prodrugs of the compounds disclosed herein are specifically contemplated. An ester may be formed from a hydroxyl functional group linked to a compound of formula (I) above by reaction with a carboxylic acid or an aminoacid. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1 to 6 carbon atoms.

The compounds of the present invention according to formula (I) above can be used for the treatment of a pathological state arising from the uncontrolled activation and/or overexpression of GSK-3β, selected from the group consisting of (i) insulin-resistance disorders; (ii) neurodegenerative diseases; (iii) mood disorders; (iv) schizophrenic disorders; (v) cancerous disorders; (vi) inflammation, (vii) osteoporosis, (viii) cardiac hypertrophy, (ix) epilepsies and (x) neuropathic pain.

Advantageously, insulin-resistance disorders are selected from the group consisting of type-2 diabetes, syndrome X, obesity and polycystic ovary syndrome.

Advantageously, acute and chronic neurodegenerative diseases are selected from the group consisting of Parkinson's disease, Alzheimer's disease and Huntington's disease.

Advantageously, mood disorders are selected from the group consisting of bipolar disorders, such as bipolar I, bipolar II, cyclothymia and bipolar disorder not otherwise specified (BD-NOS), and depressive disorders, such as atypical depression (AD), melancholic depression, psychotic major depression (PMD), catatonic depression, postpartum depression (PPD), seasonal affective disorder (SAD), dysthymia, and depressive disorder not otherwise specified (DD-NOS).

Advantageously, schizophrenic disorders are selected from the group consisting of paranoid schizophrenia, disorganized schizophrenia, catatonic schizophrenia, simple schizophrenia, residual schizophrenia, and undifferentiated schizophrenia.

Advantageously, cancerous disorders are selected from the group consisting of prostate, pancreatic, ovarian, and colon-rectal cancer and MLL-associated leukaemia.

Typically, the 1H-indazole-3-carboxamide compounds according to formula (I) useful in this invention are administered in the form of a pharmaceutical composition.

Accordingly, a further aspect of the present invention relates to a pharmaceutical composition comprising at least one compound of formula (I) as described above and at least one inert pharmaceutically acceptable excipient.

Preferably, the pharmaceutical composition of the present invention is prepared in suitable dosage forms comprising an effective amount of at least one compound of formula (I) as described above, a salt thereof with a pharmaceutically acceptable organic or inorganic acid or base, or a prodrug thereof, and at least one inert pharmaceutically acceptable excipient.

Examples of suitable dosage forms are tablets, capsules, coated tablets, granules, solutions and syrups for oral administration; solutions, pomade and ointment for topical administration; medicated patches for transdermal administration; suppositories for rectal administration and injectable sterile solutions.

Other suitable dosage forms are those with sustained release and those based on liposomes for oral, injectable or transdermal administration.

As described herein, the pharmaceutical composition of the present invention comprises a compound of the invention together with a pharmaceutically acceptable excipient, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired.

Some examples of materials which can serve as pharmaceutically acceptable excipient include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, other non-toxic compatible lubricants such as sodium lauryl sulfate and magnesium stearate, coloring agents, releasing agents, coating agents, sweetening, flavoring and perfuming agents, preservatives and antioxidants.

The terms "pharmaceutically acceptable" and "physiologically acceptable" are intended to define, without any particular limitation, any material suitable for preparing a pharmaceutical composition to be administered to a living being.

The dosage forms can also contain other traditional ingredients such as: preservatives, stabilizers, surfactants, buffers, salts for regulating osmotic pressure, emulsifiers, sweeteners, colorants, flavourings and the like.

The amount of the 1H-indazole-3-carboxamide according to formula (I) or of the pharmaceutically acceptable salt of acid addition thereof in the pharmaceutical composition of the present invention can vary over a wide range depending on known factors, for example, the type of pathology, the severity of the disease, the patient's body weight, the dosage form, the chosen route of administration, the number of administrations per day and the efficacy of the selected 1H-indazole-3-carboxamide compound according to formula (I). However, a person skilled in the art can determine the optimum amount in easily and routinely manner.

Typically, the amount of compound of formula (I) or of the pharmaceutically acceptable salt of acid addition thereof in the pharmaceutical composition of the present invention will be such as to ensure a level of administration from 0.0001 to 100 mg/kg/day. Preferably, the level of administration is from 0.001 to 50 mg/kg/day, and even more preferably from 0.01 to 10 mg/kg/day.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

The pharmaceutical compositions of this invention may be administered orally, parenterally, by inhalation spray, topically, rectally, nasally, buccally, vaginally or via an implanted reservoir. The term parenteral as used herein includes subcutaneous, intracutaneous, intravenous, intramuscular, intraarticular, intrasynovial, intrasternal, intrathecal, intralesional and intracranial injection or infusion techniques.

The pharmaceutical compositions of this invention may also be administered by nasal aerosol or inhalation or delivered by implantation (e.g., surgically), such as with an implantable or indwelling device like a stent.

The dosage forms of the pharmaceutical composition of the present invention can be prepared by techniques that are familiar to a pharmaceutical chemist, and comprise mixing, granulation, compression, dissolution, sterilization and the like.

The man skilled in the art has a well-established literature of heterocyclic and other relevant chemical transformations, recovery and purification technologies to draw upon, in combination with the information contained in the examples which follow, for guidance on synthetic strategies, protecting groups, and other materials and methods useful for the synthesis, recovery and characterization of the compounds of this invention, including compounds containing the various choices for $R_a$, Y and $R_b$.

Various synthetic approaches may be used to produce the compounds described herein, including those approaches depicted schematically below. The man skilled in the art will appreciate that protecting groups may be used in these approaches. "Protecting groups", are moieties that are used to temporarily block chemical reaction at a potentially reactive site (e.g., an amine, hydroxyl, thiol, aldehyde, etc.) so that a reaction can be carried out selectively at another site in a multifunctional compound. In preferred embodiments, a protecting group reacts selectively in good yield to give a protected substrate that is suitable for the planned reactions; the protecting group should be selectively removable in good yield by readily available, preferably nontoxic reagents that do not unduly attack the other functional groups present; the protecting group preferably forms an readily separable derivative (more preferably without the generation of new stereogenic centers); and the protecting group preferably has a minimum of additional functionality to avoid the complication of further sites of reaction. A wide variety of protecting groups and strategies, reagents and conditions for deploying and removing them are known in the art.

Also, one may chose reagents enriched for a desired isotope, e.g. tritium in place of hydrogen, to create compounds of this invention containing such isotope(s). Compounds containing tritium in place of hydrogen in one or more locations, or containing various isotopes of C, N, P and O, are encompassed by this invention and may be used, for instance, for studying metabolism and/or tissue distribution of the compounds or to alter the rate or path of metabolism or other aspects of biological functioning. The compounds of the this invention can be synthesized using the methods described below, together with synthetic methods known in the art of synthetic organic chemistry, or by a variation thereon as appreciated by those skilled in the art. Preferred methods include, but are not limited to those described below. The reactions are performed in a solvent appropriate to the reagents and materials employed and suitable for the transformation being effected.

It will be understood by those skilled in the art of organic synthesis that the functionality present on the molecule should be consistent the transformations proposed. This will sometimes require some judgment to modify the order of the synthetic steps or to select one particular process scheme over another in order to obtain a desired compound of the invention.

Non-limiting examples of compounds of formula (I) according to the present invention are those of the following Table A.

TABLE A
| Example | Structural Formula |
|---------|-------------------|
| 1 | 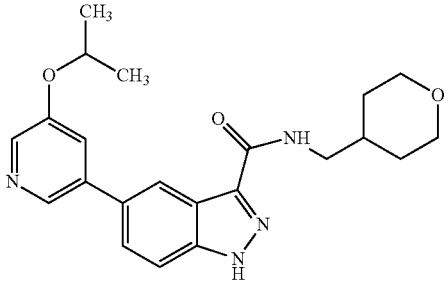 [SMILES: CC(C)Oc1cncc(-c2ccc3[nH]nc(C(=O)NCC4CCOCC4)c3c2)c1] |
| 2 | 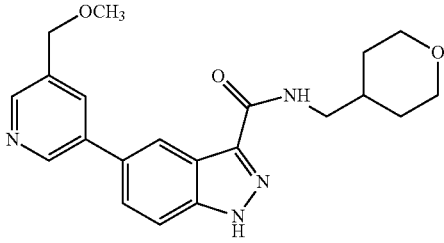 [SMILES: COCc1cncc(-c2ccc3[nH]nc(C(=O)NCC4CCOCC4)c3c2)c1] |
| 3 | 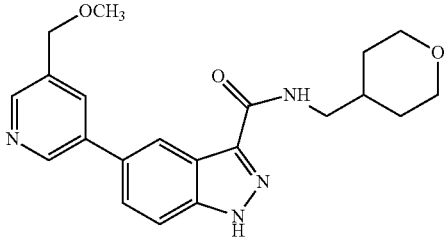 [SMILES: COCc1cncc(-c2ccc3[nH]nc(C(=O)NCC4CCOCC4)c3c2)c1] |
| 4 | 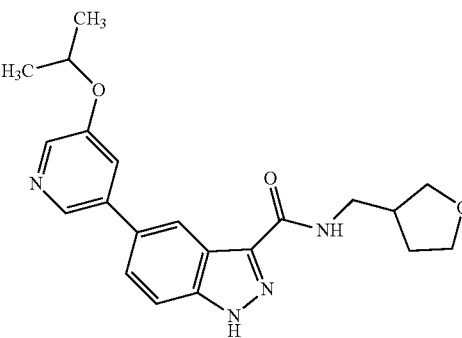 [SMILES: CC(C)Oc1cncc(-c2ccc3[nH]nc(C(=O)NCC4CCOC4)c3c2)c1] |
| 5 | 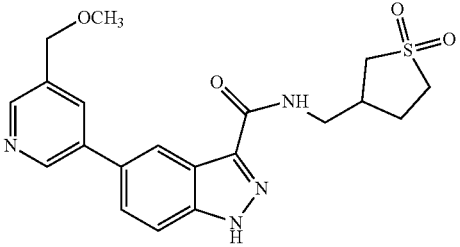 [SMILES: COCc1cncc(-c2ccc3[nH]nc(C(=O)NCC4CCS(=O)(=O)C4)c3c2)c1] |

TABLE A-continued
| Example | Structural Formula |
|---|---|
| 6 | 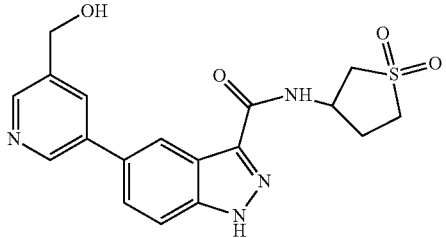 [SMILES: O=C(NC1CCS(=O)(=O)C1)c1n[nH]c2ccc(-c3cncc(CO)c3)cc12] |
| 7 | 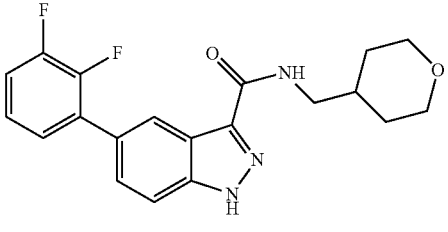 [SMILES: O=C(NCC1CCOCC1)c1n[nH]c2ccc(-c3cccc(F)c3F)cc12] |
| 8 | 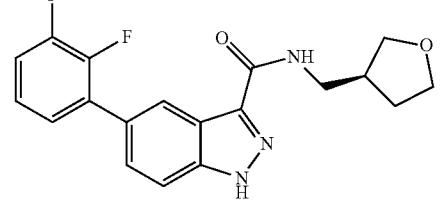 |
| 9 | 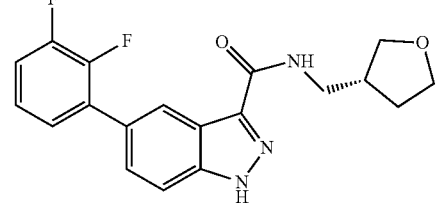 |
| 10 | 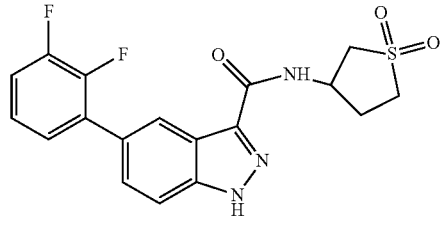 [SMILES: O=C(NC1CCS(=O)(=O)C1)c1n[nH]c2ccc(-c3cccc(F)c3F)cc12] |
| 11 | 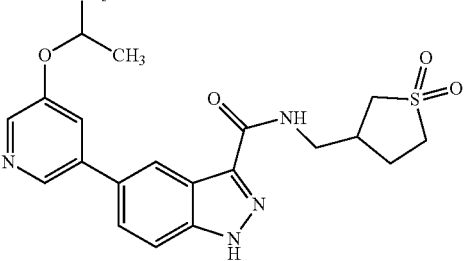 |

TABLE A-continued

| Example | Structural Formula |
| --- | --- |
| 12 | 5-(2,3-difluorophenyl)-N-((tetrahydro-2H-pyran-3-yl)methyl)-1H-indazole-3-carboxamide |
| 13 | 5-(2,3-difluorophenyl)-N-((tetrahydrofuran-2-yl)methyl)-1H-indazole-3-carboxamide |
| 14 | 5-(2,3-difluorophenyl)-N-((tetrahydro-2H-pyran-2-yl)methyl)-1H-indazole-3-carboxamide |
| 15 | 5-(2,3-difluorophenyl)-N-((tetrahydrofuran-3-yl)methyl)-1H-indazole-3-carboxamide |
| 16 | 5-(5-((dimethylamino)methyl)pyridin-3-yl)-N-((tetrahydro-2H-pyran-4-yl)methyl)-1H-indazole-3-carboxamide |

TABLE A-continued

| Example | Structural Formula |
| --- | --- |
| 17 | |
| 18 | |
| 19 | |
| 20 | |
| 21 | |

TABLE A-continued
| Example | Structural Formula |
|---------|-------------------|
| 22 | 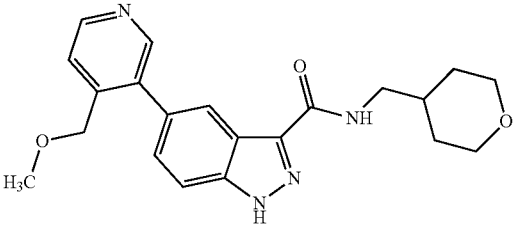 [SMILES: COCc1ccncc1-c1ccc2[nH]nc(C(=O)NCC3CCOCC3)c2c1] |
| 23 | 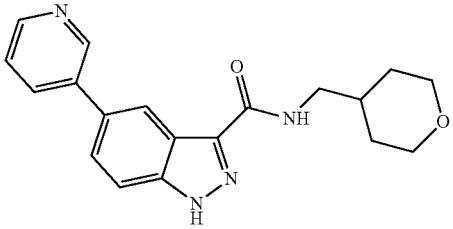 [SMILES: O=C(NCC1CCOCC1)c1n[nH]c2ccc(-c3cccnc3)cc12] |
| 24 | 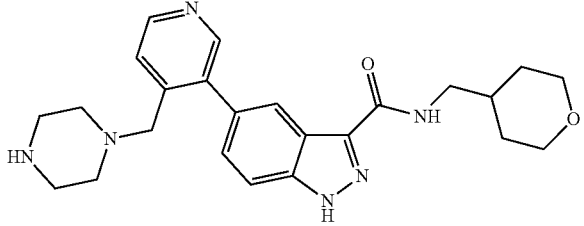 [SMILES: O=C(NCC1CCOCC1)c1n[nH]c2ccc(-c3cnccc3CN3CCNCC3)cc12] |
| 25 | 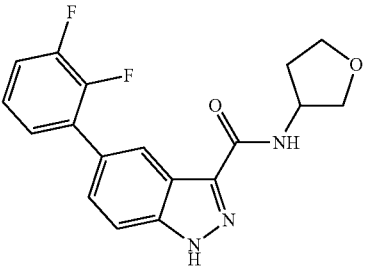 [SMILES: O=C(NC1CCOC1)c1n[nH]c2ccc(-c3cccc(F)c3F)cc12] |
| 27 | 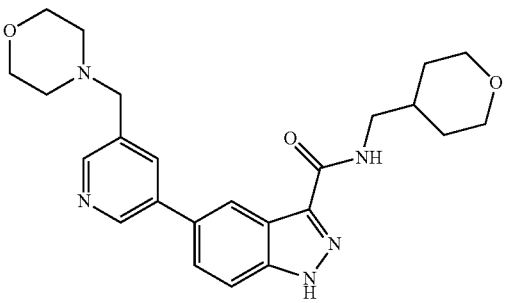 [SMILES: O=C(NCC1CCOCC1)c1n[nH]c2ccc(-c3cncc(CN4CCOCC4)c3)cc12] |
| 28 | 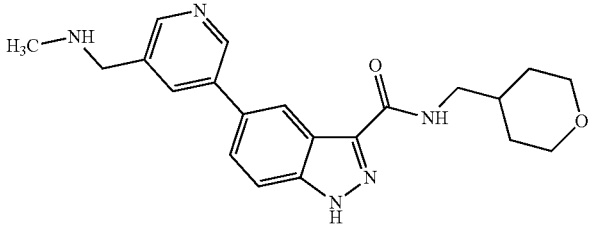 [SMILES: CNCc1cncc(-c2ccc3[nH]nc(C(=O)NCC4CCOCC4)c3c2)c1] |

EXPERIMENTAL PART $^1$H-NMR spectroscopy: internal standard=Tetramethylsilane; DMSO-$d_6$=deuterated dimethyl sulfoxide; (s)=singlet; (d)=doublet; (t)=triplet; (br)=broad; (dd)=double doublet; (dt)=double triplet; (ddd)=double double doublet; (dtd)=double triple doublet; (m)=multiplet; J=coupling constant; δ=chemical shift (in ppm).

Preparation of Compounds of Formula (I)

Compounds of Formula (I) can be obtained by application of the chemical transformations reported in general procedures A, B, C and D herein described.

General Procedure A: Synthesis of Intermediates IV and V

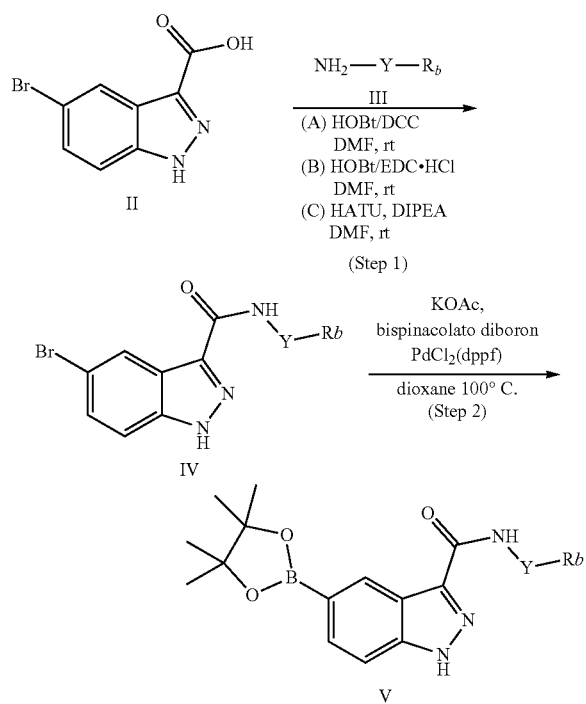

Step 1

Method (A): HOBt (1.1 eq.) and DCC (1.07 eq.) were added to a solution of 5-bromo-1H-indazole-3-carboxylic acid (II, 1 eq.) in DMF at 0° C. After 1 hour, a solution of the proper amine (III, 1.2 eq.) was added at the same temperature. The mixture was stirred at 0° C. for 2 hours and left to reach room temperature overnight. The reaction was checked by HPLC/MS. Then the mixture was concentrated and diluted with EtOAc, washed with aqueous 2N NaOH solution and with brine. The organic phase was dried over anhydrous MgSO$_4$, filtered and evaporated under reduced pressure to give the intermediate compound having general formula IV. Purification by flash chromatography was performed when required.

Method (B): A mixture of 5-bromo-1H-indazole-3-carboxylic acid (II, 1 eq.), the proper amine (III, 1-1.2 eq.), HOBt (1.2 eq.) and EDC.HCl (1.2 eq.) in DMF was stirred at room temperature overnight. The reaction was checked by HPLC/MS. The mixture was concentrated and then diluted with EtOAc. The solution was washed with aqueous 2N NaOH solution and with brine. The organic phase was dried over anhydrous MgSO$_4$, filtered and evaporated under reduced pressure to give the intermediate compound having general formula IV. Purification by flash chromatography was performed when required.

Method (C): To a solution of 5-bromo-1H-indazole-3-carboxylic acid II (1 eq.) in dry DMF under Ar atmosphere, the proper amine (III, 1.2 eq.), DIPEA (4.5 eq.) and HATU (1.2 eq.) were added. After stirring at room temperature overnight, the solvent was evaporated under reduced pressure. The residue was diluted with DCM and washed with water. The aqueous layer was extracted with DCM. The combined organic layers were dried over anhydrous Na$_2$SO$_4$, filtered and evaporated under reduced pressure to give the intermediate compound having general formula IV. Purification by flash chromatography was performed when required.

5-Bromo-N-((tetrahydro-2H-pyran-4-yl)methyl)-1H-indazole-3-carboxamide (IVa). The title compound was obtained according to general procedure A, step 1, method (A) using 5-bromo-1H-indazole-3-carboxylic acid (II, 0.1 g, 0.415 mmol), (tetrahydro-2H-pyran-4-yl)methanamine (IIIa, 0.055 g, 0.481 mmol), HOBt (0.062 g, 0.456 mmol), DCC (0.092 g, 0.444 mmol). The crude was purified by flash chromatography (SiO$_2$, DCM/MeOH), affording 0.11 g of the title product. Yield=69%. HPLC-MS (ESI) m/z: 338.1 [M-H]$^+$.

5-Bromo-N-(1,1-dioxidotetrahydrothiophen-3-yl)-1H-indazole-3-carboxamide (IVb). The title compound was obtained according to general procedure A, step 1, method (B) using 5-bromo-1H-indazole-3-carboxylic acid (II, 0.3 g, 1.245 mmol), 3-aminotetrahydrothiophene 1,1-dioxide (IIIb, 0.168 g, 1.245 mmol), HOBt (0.202 g, 1.494 mmol), EDC.HCl (0.286 g, 1.494 mmol). The crude (0.22 g) was used in the next step without further purification. Yield=49%. HPLC-MS (ESI) m/z: 359.9 [M-H]$^+$.

5-Bromo-N-((tetrahydrofuran-2-yl)methyl)-1H-indazole-3-carboxamide (IVc). The title compound was obtained according to general procedure A, step 1, method (B) using 5-bromo-1H-indazole-3-carboxylic acid (II, 0.2 g, 0.830 mmol), (tetrahydrofuran-2-yl)methanamine (IIIc, 0.084 g, 0.830 mmol), HOBt (0.135 g, 0.996 mmol), EDC.HCl (0.191 g, 0.996 mmol). The crude (0.16 g) was used in the next step without further purification. Yield=59%. HPLC-MS (ESI) m/z: 326.0 [M-H]$^+$.

5-Bromo-N-((tetrahydro-2H-pyran-2-yl)methyl)-1H-indazole-3-carboxamide (IVd). The title compound was obtained according to general procedure A, step 1, method (B) using 5-bromo-1H-indazole-3-carboxylic acid (II, 0.2 g, 0.830 mmol), (tetrahydro-2H-pyran-2-yl)methanamine (IIId, 0.096 g, 0.830 mmol), HOBt (0.135 g, 0.996 mmol), EDC.HCl (0.191 g, 0.996 mmol). The crude (0.15 g) was used in the next step without further purification. Yield=40%. HPLC-MS (ESI) m/z: 340.0 [M-H]$^+$.

5-Bromo-N-((tetrahydrofuran-3-yl)methyl)-1H-indazole-3-carboxamide (IVe). The title compound was obtained according to general procedure A, step 1, method (B) using 5-bromo-1H-indazole-3-carboxylic acid (II, 0.2 g, 0.830 mmol), (tetrahydrofuran-3-yl)methanamine (IIIe, 0.084 g, 0.830 mmol), HOBt (0.135 g, 0.996 mmol), EDC.HCl (0.191 g, 0.996 mmol). The crude (0.27 g) was used in the next step without further purification. Yield=29%. HPLC-MS (ESI) m/z: 326.0 [M-H]$^+$.

5-bromo-N-(tetrahydrofuran-3-yl)-1H-indazole-3-carboxamide (IVf). The title compound was obtained according to general procedure A, step 1, method (B) using 5-bromo-1H-indazole-3-carboxylic acid (II, 0.3 g, 1.245 mmol), tetrahydrofuran-3-amine (IIIf, 0.108 g, 1.245 mmol), HOBt (0.20 g, 1.494 mmol), EDC.HCl (0.29 g, 1.494 mmol). The crude (0.30 g) was used in the next step without further purification. Yield=77%. HPLC-MS (ESI) m/z: 311.1 [M-H]⁺.

5-bromo-N-(tetrahydro-2H-pyran-3-yl)-1H-indazole-3-carboxamide (IVg). The title compound was obtained according to general procedure A, step 1, method (B) using 5-bromo-1H-indazole-3-carboxylic acid (II, 0.4 g, 1.66 mmol), tetrahydro-2H-pyran-3-amine hydrochloride (IIIg, 0.274 g, 1.991 mmol), HOBt (0.27 g, 1.991 mmol), EDC.HCl (0.38 g, 1.991 mmol). The crude was purified by flash chromatography (SiO₂, Cyclohexane/EtOAc), affording 0.13 g of the title product. Yield=21%. HPLC-MS (ESI) m/z: 326.0 [M-H]⁺.

5-bromo-N-[(1,1-dioxo-1λ⁶-thiolan-3-yl)methyl]-1H-indazole-3-carboxamide (IVh). The title compound was obtained according to general procedure A, step 1, method (C) using 5-bromo-1H-indazole-3-carboxylic acid (II, 0.25 g, 1.3 mmol), 3-(aminomethyl)-1λ⁶-thiolane-1,1-dione (IIIh, 0.23 g, 1.991 mmol), DIPEA (0.98 ml, 5.6 mmol), and HATU (0.47 g, 1.3 mmol) The crude was purified by flash chromatography (SiO₂, DCM/MeOH), affording 0.23 g of the title product. Yield=60%. HPLC-MS (ESI) m/z: 371 [M-H]⁺.

Step 2

A mixture of compound IV (1 eq.), bis(pinacolato)diboron (3 eq.) and KOAc (2 eq.) in 1,4-dioxane was first degassed with a N₂ stream for 10 minutes and then added with PdCl₂(dppf) (0.2 eq.). After purging again with N₂, the mixture was stirred at 100° C. overnight, then diluted with MeOH and filtered through Celite to remove the insoluble solids. The solvent was evaporated under reduced pressure and the residue was purified by flash chromatography to give the intermediate compound with formula V.

N-((tetrahydro-2H-pyran-4-yl)methyl)-5-(4,4,5,5-tetramethyl-1,3,2-dioxaborolan-2-yl)-1H-indazole-3-carboxamide (Va). The title compound was obtained according to general procedure A, step 2 using 5-bromo-N-((tetrahydro-2H-pyran-4-yl)methyl)-1H-indazole-3-carboxamide (IVa, 1.5 g, 4.4 mmol), bis(pinacolato)diboron (3.4 g, 13 mmol), KOAc (0.87 g, 8.9 mmol), PdCl₂(dppf) (0.65 g, 0.89 mmol). The crude was purified by flash chromatography (SiO₂, DCM/MeOH) to obtain 0.77 g of the title product. Yield=45%. HPLC-MS (ESI) m/z: 326.1 [M-H]⁺.

N☐(1,1☐dioxo☐1λ⁶☐thiolan☐3☐yl)☐5☐(4,4,5,5☐tetramethyl☐1,3,2☐dioxaborolan☐2☐yl)☐1H☐indazole☐3☐carboxamide (Vb). The title compound was obtained according to general procedure A, step 2 using 5-bromo-N-(1,1-dioxidotetrahydrothiophen-3-yl)-1H-indazole-3-carboxamide (IVb, 0.2 g, 0.6 mmol), bis(pinacolato)diboron (0.4 g, 1.7 mmol), KOAc (0.11 g, 1.2 mmol), PdCl₂(dppf) (0.08 g, 0.1 mmol). The crude was purified by flash chromatography (SiO₂, DCM/MeOH) to obtain 0.23 g of the title product. Yield=100%. HPLC-MS (ESI) m/z: 406.1 [M-H]⁺.

N-[(1,1-dioxo-1λ⁶-thiolan-3-yl)methyl]-5-(4,4,5,5-tetramethyl-1,3,2-dioxaborolan-2-yl)-1H-indazole-3-carboxamide (Vc). The title compound was obtained according to general procedure A, step 2 using 5-bromo-N-[(1,1-dioxo-1λ⁶-thiolan-3-yl)methyl]-1H-indazole-3-carboxamide (IVh, 0.2 g, 0.6 mmol), bis(pinacolato)diboron (0.4 g, 1.7 mmol), KOAc (0.11 g, 1.2 mmol), PdCl₂(dppf) (0.08 g, 0.1 mmol). The crude was purified by flash chromatography (SiO₂, DCM/MeOH) to obtain 0.24 g of the title product. Yield=100%. HPLC-MS (ESI) m/z: 420.1 [M-H]⁺.

General Procedure B: Synthesis of Intermediates
$R_a$—Br (VI-VIII, X) and $R_a$—B(OR)₂ (XI)

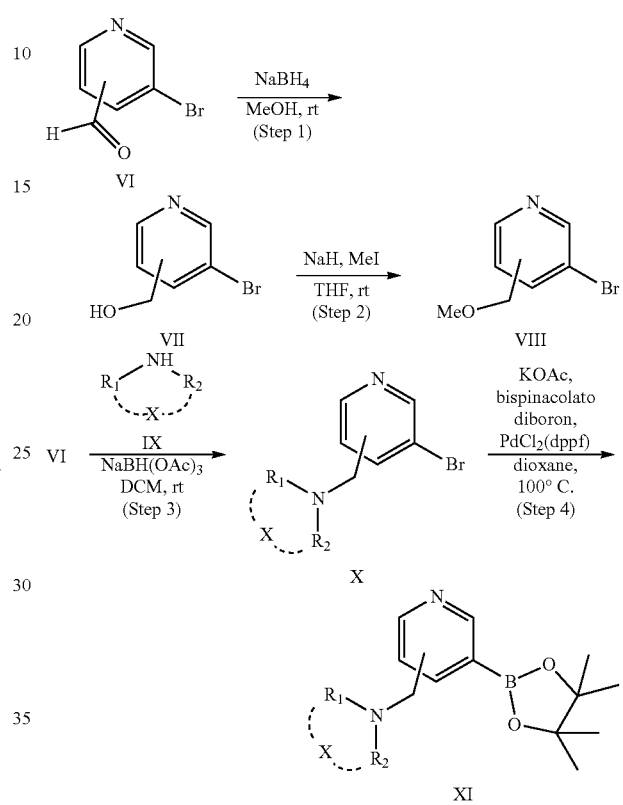

Step 1

To a solution of the proper bromopyridine-carbaldehyde (VI, 1 eq.) in MeOH, NaBH₄ (2 eq.) was added portionwise. The mixture was stirred at room temperature for 3 hours. After this time, water was added and the mixture was concentrated under vacuum. The residue was diluted with water and extracted with DCM. The combined organic phases were dried over anhydrous MgSO₄, filtered and evaporated under reduced pressure to give the intermediate compound having general formula VII, which was used in the next step without further purification.

(5-Bromopyridin-3-yl)methanol (VIIa). The title compound was obtained according to general procedure B, step 1 using 5-bromopyridine-3-carbaldehyde (VIa, 0.25 g, 1.34 mmol), NaBH₄ (0.10 g, 2.69 mmol). The crude (0.15 g) was used in the next step without further purification. Yield=60%.

(3-Bromopyridin-4-yl)methanol (VIIb). The title compound was obtained according to general procedure B, step 1 using 3-bromopyridine-4-carbaldehyde (VIb, 0.25 g, 1.34 mmol), NaBH₄ (0.10 g, 2.69 mmol). The crude (0.17 g) was used in the next step without further purification. Yield=69%.

Step 2

To a solution of the proper bromopyridine-methanol (VII, 1 eq.) in THF, NaH 60% (2 eq.) was added at 0° C. The mixture was stirred at 0° C. for 30 minutes. After this time, MeI (1.2 eq.) was added and the mixture was stirred at room temperature overnight. The mixture was diluted with water and extracted with $Et_2O$. The combined organic phases were dried over anhydrous $MgSO_4$, filtered and evaporated under reduced pressure to give the intermediate compound having general formula VIII, which was used for the next step without further purification.

3-Bromo-5-(methoxymethyl)pyridine (VIIIa). The title compound was obtained according to general procedure B, step 2 using (5-bromopyridin-3-yl)methanol (VIIa, 0.15 g, 0.81 mmol), NaH 60% (0.06 g, 1.62 mmol), MeI (0.06 mL, 0.97 mmol). The crude (0.12 g) was used in the next step without further purification. Yield=70%.

3-Bromo-4-(methoxymethyl)pyridine (VIIIb). The title compound was obtained according to general procedure B, step 2 using (3-bromopyridin-4-yl)methanol (VIIb, 0.17 g, 0.92 mmol), NaH 60% (0.07 g, 1.84 mmol), MeI (0.07 mL, 1.10 mmol). The crude (0.12 g) was used in the next step without further purification. Yield=62%.

Step 3

A solution of the proper bromopyridine-carbaldehyde (VI, 1 eq.) and amine (IX, 1-5 eq.) in DCM was stirred at room temperature for 2 hours. After this time, $NaBH(OAc)_3$ (1.5 eq.) was added. The mixture was stirred at room temperature overnight. The reaction was controlled by HPLC/MS. The residue was diluted with aqueous 1N NaOH solution, stirred for 1 hours, and extracted with DCM. The combined organic phases were dried over anhydrous $MgSO_4$, filtered and evaporated under reduced pressure to give the intermediate compound having general formula X, which was used for the next step without further purification.

1-(5-Bromopyridin-3-yl)-N,N-dimethylmethanamine (Xa). The title compound was obtained according to general procedure B, step 3 using 5-bromopyridine-3-carbaldehyde (VIa, 0.25 g, 1.34 mmol), dimethylamine (IXa, 0.064 g, 1.41 mmol), $NaBH(OAc)_3$ (0.43 g, mmol). The crude (0.24 g) was used in the next step without further purification. Yield=83%. HPLC-MS (ESI) m/z: 217.0 $[M-H]^+$.

3-Bromo-5-[(pyrrolidin-1-yl)methyl]pyridine (Xb). The title compound was obtained according to general procedure B, step 3 using 5-bromopyridine-3-carbaldehyde (Va, 0.25 g, 1.34 mmol), pyrrolidine (IXb, 0.10 g, 1.41 mmol), $NaBH(OAc)_3$ (0.43 g, 2 mmol). The crude (0.29 g) was used in the next step without further purification. Yield=89%. HPLC-MS (ESI) m/z: 243.0 $[M-H]^+$.

3-Bromo-4-[(pyrrolidin-1-yl)methyl]pyridine (Xc). The title compound was obtained according to general procedure B, step 3 using 3-bromopyridine-4-carbaldehyde (Vb, 0.25 g, 1.34 mmol), pyrrolidine (IXb, 0.12 g, 1.74 mmol), $NaBH(OAc)_3$ (0.43 g, 2 mmol). The crude (0.32 g) was used in the next step without further purification. Yield=73%. HPLC-MS (ESI) m/z: 243.0 $[M-H]^+$.

4-[(3-Bromopyridin-4-yl)methyl]morpholine (Xd). The title compound was obtained according to general procedure B, step 3 using 3-bromopyridine-4-carbaldehyde (Vb, 0.25 g, 1.34 mmol), morpholine (IXc, 0.15 g, 1.74 mmol), $NaBH(OAc)_3$ (0.43 g, 2 mmol). The crude (0.37 g) was used in the next step without further purification. Yield=99%. HPLC-MS (ESI) m/z: 258.9 $[M-H]^+$.

1-(3-Bromopyridin-4-yl)-N,N-dimethylmethanamine (Xe). The title compound was obtained according to general procedure B, step 3 using 3-bromopyridine-4-carbaldehyde (VIb, 0.5 g, 2.69 mmol), dimethylamine (IXa, 6.72 mL, 13.44 mmol), $NaBH(OAc)_3$ (0.86 g, 4 mmol). The crude (0.56 g) was used in the next step without further purification. Yield=82%. HPLC-MS (ESI) m/z: 217.0 $[M-H]^+$.

Tert-butyl 4-[(3-bromopyridin-4-yl)methyl]piperazine-1-carboxylate (Xf). The title compound was obtained according to general procedure B, step 3 using 3-bromopyridine-4-carbaldehyde (Vb, 0.25 g, 1.34 mmol), N-Boc-piperazine (IXd, 0.25 g, 1.34 mmol), $NaBH(OAc)_3$ (0.12 g, 2.02 mmol). The crude (0.36 g) was used in the next step without further purification. Yield=76%. HPLC-MS (ESI) m/z: 358.1 $[M-H]^+$.

4-((5-Bromopyridin-3-yl)methyl)morpholine (Xg). The title compound was obtained according to general procedure B, step 3 using 5-bromopyridine-3-carbaldehyde (VIa, 0.25 g, 1.34 mmol), morpholine (IXc, 0.12 g, 1.34 mmol), $NaBH(OAc)_3$ (0.43 g, 2 mmol). The crude (0.32 g) was used in the next step without further purification. Yield=78%. HPLC-MS (ESI) m/z: 258.9 $[M-H]^+$.

1-(5-Bromopyridin-3-yl)-N-methylmethanamine (Xh). The title compound was obtained according to general procedure B, step 3 using 5-bromopyridine-3-carbaldehyde (VIa, 0.25 g, 1.34 mmol), methanamine (IXe, 0.63 g, 6.72 mmol), $NaBH(OAc)_3$ (0.43 g, 2 mmol). The crude (0.085 g) was used in the next step without further purification. Yield=99%. HPLC-MS (ESI) m/z: 202.0 $[M-H]^+$.

Step 4

A mixture of compound X (1 eq.), bis(pinacolato)diboron (1.5 eq.) and KOAc (3 eq.) in 1,4-dioxane was placed in a Schlenk tube. The resulting mixture was degassed with $N_2$ for 10 minutes. Then, $PdCl_2(dppf)$ (0.2 eq.) was added and the mixture was heated at 100° C. overnight. Conversion was checked by HPLC/MS. The mixture was diluted with EtOAc/MeOH and the insoluble solids were removed by filtration through Celite. The solvent was evaporated under reduced pressure and the residue was purified by flash chromatography to give intermediate having general formula XI.

Tert-butyl-4-{[3-(4,4,5,5-tetramethyl-1,3,2-dioxaborolan-2-yl)pyridin-4-yl]methyl}piperazine-1-carboxylate (Xa). The title compound was obtained according to general procedure B, step 4 using tert-butyl 4-[(3-bromopyridin-4-yl)methyl]piperazine-1-carboxylate (Xf, 2.5 g, 7.02 mmol), bis(pinacolato)diboron (2.67 g, 10.53 mmol), KOAc (2.06 g, 21.05 mmol), $PdCl_2(dppf)$ (1.14 g, 1.40 mmol). The crude was purified by flash chromatography ($SiO_2$, $CHCl_3$/MeOH) to give 1.23 g of the title product. Yield=50%. HPLC-MS (ESI) m/z: 404.1 $[M-H]^+$.

4-((5-(4,4,5,5-Tetramethyl-1,3,2-dioxaborolan-2-yl)pyridin-3-yl)methyl)morpholine (XIb). The title compound was obtained according to general procedure B, step 4 using 4-((5-bromopyridin-3-yl)methyl)morpholine (Xg, 0.317 g, 1.23 mmol), bis(pinacolato)diboron (0.626 g, 2.47 mmol), KOAc (0.242 g, 2.47 mmol), $PdCl_2(dppf)$ (0.201 g, 0.25 mmol). The crude (0.827 g) was used in the next step without further purification. Yield=99%. HPLC-MS (ESI) m/z: 305.0 $[M-H]^+$.

General Procedure C: Synthesis of Compounds I
(Examples 1-11, and 13-28)

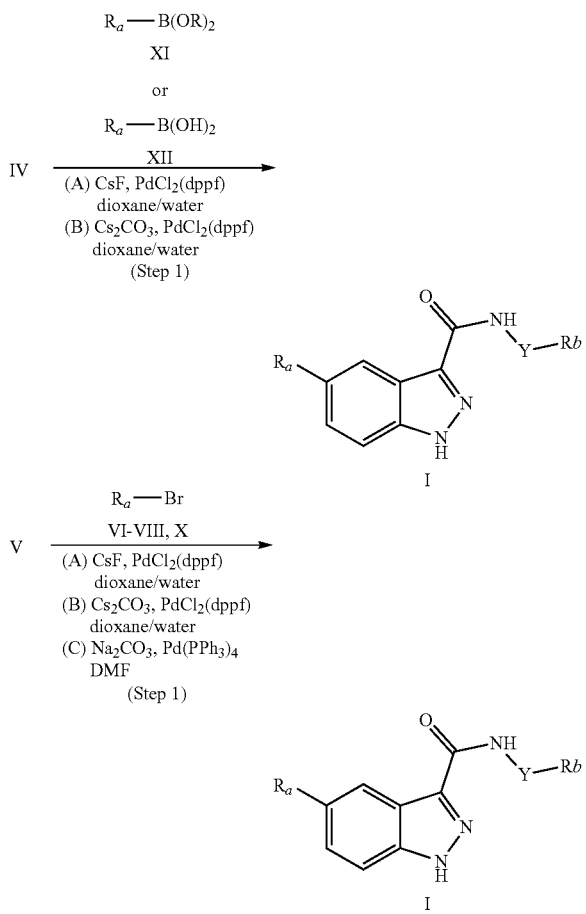

Step 1

Method (A): A mixture of the proper intermediate IV or V (1 eq.), intermediate $R_a$—B(OR)$_2$ (XI, 2 eq.), $R_a$—B(OH)$_2$ (XII, 2 eq.) or $R_a$—Br (VI-VIII, X, 1.2-2 eq.) and CsF (2 eq.) in 1,4-dioxane and water (4:1) was placed in a Schlenk tube. The resulting mixture was degassed with $N_2$ for 10 minutes. Then, PdCl$_2$(dppf) (0.05-0.2 eq.) was added and the mixture was heated at 100° C. overnight. Conversion was checked by HPLC/MS. The mixture was diluted with MeOH and then the insoluble solids were removed by filtration through Celite. The solvent was evaporated under reduced pressure and the residue was purified by flash chromatography to give the final compound having general formula I.

Method (B): A mixture of the proper intermediate IV or V (1 eq.), intermediate $R_a$—B(OH)$_2$ (XII, 1.3-4 eq.) or $R_a$—Br (VI-VIII, X, 1.1 eq.) and Cs$_2$CO$_3$ (1.3-4 eq.) in 1,4-dioxane/water (4:1) was placed in a Schlenk tube. The resulting mixture was degassed with $N_2$ for 10 minutes. Then, PdCl$_2$(dppf) (0.08-0.25 eq.) was added and the mixture was heated in the microwave at 130° C. for 15 minutes. Conversion was checked by HPLC/MS. The mixture was diluted with EtOAc/MeOH and then the insoluble solids were removed by filtration through Celite. The solvent was evaporated under reduced pressure and the residue was purified by flash chromatography to give the final compound having general formula I.

Method (C): A mixture of the proper intermediate IV or V (1 eq.), intermediate $R_a$—B(OH)$_2$ (XII, 2 eq.) or $R_a$—Br (VI-VIII, X, 1.1 eq.) and aqueous 2N Na$_2$CO$_3$ solution (1.1 eq.) in DMF was placed in a Schlenk tube. The resulting mixture was degassed with $N_2$ for 10 minutes. Then, Pd(PPh$_3$)$_4$ (0.05 eq.) was added and the mixture was heated at 100° C. overnight. Conversion was checked by HPLC/MS. The mixture was diluted with EtOAc/MeOH and then the insoluble solids were removed by filtration through Celite. The solvent was evaporated under reduced pressure and the residue was purified by flash chromatography to give the final compound having general formula I.

5-(5-Isopropoxypyridin-3-yl)-N-((tetrahydro-2H-pyran-4-yl)methyl)-1H-indazole-3-carboxamide (Example 1). The title compound was obtained according to general procedure C, step 1, method (A) using 5-bromo-N-((tetrahydro-2H-pyran-4-yl)methyl)-1H-indazole-3-carboxamide (IVa, 0.1 g, 0.296 mmol), (5-isopropoxypyridin-3-yl)boronic acid (XIIa, 0.080 g, 0.44 mmol), CsF (0.09 g, 0.59 mmol), PdCl$_2$(dppf) (0.024 g, 0.030 mmol). The crude was purified by flash chromatography (SiO$_2$, DCM/MeOH) to give 0.07 g of the title product. Yield=63%. HPLC-MS (ESI) m/z: 395.1 [M-H]$^+$. $^1$H NMR (400 MHz, CD$_3$OD): δ 8.77 (s, 1H), 8.65 (s, 1H), 8.54-8.50 (m, 1H), 8.47-8.44 (m, 1H), 7.88-7.82 (m, 1H), 7.82-7.77 (m, 1H), 5.07-4.98 (m, 1H), 4.01-3.92 (m, 2H), 3.47-3.36 (m, 4H), 2.00-1.90 (m, 1H), 1.77-1.69 (m, 2H), 1.47 (d, J=6.0 Hz, 6H), 1.45-1.33 (m, 2H).

5-(5-(Methoxymethyl)pyridin-3-yl)-N-((tetrahydro-2H-pyran-4-yl)methyl)-1H-indazole-3-carboxamide (Example 2). The title compound was obtained according to general procedure C, step 1, method (A) using N-((tetrahydro-2H-pyran-4-yl)methyl)-5-(4,4,5,5-tetramethyl-1,3,2-dioxaborolan-2-yl)-1H-indazole-3-carboxamide (Va, 0.2 g, 0.29 mmol), 3-bromo-5-(methoxymethyl)pyridine (VIIIa, 0.12 g, 0.57 mmol), CsF (0.087 g, 0.57 mmol), PdCl$_2$(dppf) (0.012 g, 0.014 mmol). The crude was purified by reverse phase chromatography (C18, NH$_4$HCO$_3$/ACN) to give 0.015 g of the title product. Yield=13%. HPLC-MS (ESI) m/z: 381.1 [M-H]$^+$. $^1$H NMR (400 MHz, CD$_3$OD): δ 8.79 (d, J=2.2 Hz, 1H), 8.54-8.47 (m, 2H), 8.13 (t, J=2.1 Hz, 1H), 7.80-7.68 (m, 2H), 4.59 (s, 2H), 3.95 (dd, J=11.5 Hz, 2.6 Hz, 2H), 3.46 (s, 3H), 3.45-3.38 (m, 2H), 3.35 (d, J=7.0 Hz, 2H), 1.99-1.88 (m, 1H), 1.75-1.68 (m, 2H), 1.44-1.31 (m, 2H).

5-(5-(Hydroxymethyl)pyridin-3-yl)-N-((tetrahydro-2H-pyran-4-yl)methyl)-1H-indazole-3-carboxamide (Example 3). The title compound was obtained according to general procedure C, step 1, method (A) using N-((tetrahydro-2H-pyran-4-yl)methyl)-5-(4,4,5,5-tetramethyl-1,3,2-dioxaborolan-2-yl)-1H-indazole-3-carboxamide (Va, 0.1 g, 0.26 mmol), (5-bromopyridin-3-yl)methanol (VIIa, 0.098 g, 0.52 mmol), CsF (0.079 g, 0.52 mmol), PdCl$_2$(dppf) (0.019 g, 0.026 mmol). The crude was purified by reverse phase chromatography (C18, NH$_4$HCO$_3$/ACN) to give 0.013 g of the title product. Yield=13%. HPLC-MS (ESI) m/z: 367.1 [M-H]$^+$. $^1$H NMR (400 MHz, CD$_3$OD): δ 8.78 (t, J=2.0 Hz, 1H), 8.52 (m, 2H), 8.14 (m, 1H), 7.73 (m, 2H), 4.76 (s, 2H), 3.96 (dd, J=11.2 and 2.8 Hz, 2H), 3.42 (td, J=12.0 and 2.4 Hz, 2H), 3.36 (d, J=7.2 Hz, 2H), 1.94 (m, 1H), 1.73 (dd, J=12.3 and 2.0 Hz, 2H), 1.38 (m, 2H).

5-(5-Isopropoxypyridin-3-yl)-N-((tetrahydrofuran-3-yl)methyl)-1H-indazole-3-carboxamide (Example 4). The title compound was obtained according to general procedure C, step 1, method (A) using 5-bromo-N-((tetrahydrofuran-3-yl)methyl)-1H-indazole-3-carboxamide (IVe, 0.140 g, 0.40 mmol), (5-isopropoxypyridin-3-yl)boronic acid (XIIa, 0.136 g, 0.50 mmol), CsF (0.131 g, 1.1 mmol), PdCl$_2$(dppf) (0.076 g, 0.1 mmol). The crude was purified by flash chromatography (SiO$_2$, DCM/MeOH) to give 0.1 g of the title product. Yield=52%. HPLC-MS (ESI) m/z: 380.4 [M-H]$^+$. $^1$H NMR (300 MHz, CDCl$_3$): δ 10.67 (s, 1H), 8.65 (dd, J=1.7, 0.9 Hz, 1H), 8.53 (d, J=1.9 Hz, 1H), 8.30 (d, J=2.7 Hz, 1H), 7.71 (dd, J=8.8, 1.7 Hz, 1H), 7.63 (dd, J=8.8, 0.9 Hz, 1H), 7.55-7.47 (m, 1H), 7.33 (d, J=6.1 Hz, 0H), 4.73 (dq, J=12.1, 6.1 Hz, 1H), 4.05-3.87 (m, 2H), 3.82 (td, J=8.2, 6.9 Hz, 1H), 3.71 (dd, J=8.8, 5.2 Hz, 1H), 3.69-3.47 (m, 2H), 2.76-2.65 (m, 1H), 2.22-2.06 (m, 2H), 1.78 (td, J=12.8, 6.9 Hz, 2H), 1.42 (d, J=6.1 Hz, 6H).

5-(5-(Methoxymethyl)pyridin-3-yl)-N-(1,1-dioxidotetrahydrothiophen-3-yl)methyl)-1H-indazole-3-carboxamide (Example 5). The title compound was obtained according to general procedure C, step 1, method (A) using N-[(1,1-dioxo-1λ$^6$-thiolan-3-yl)methyl]-5-(4,4,5,5-tetramethyl-1,3,2-dioxaborolan-2-yl)-1H-indazole-3-carboxamide (Vc 0.23 g, 0.6 mmol), 3-bromo-5-(methoxymethyl)pyridine (VIIIa, 0.12 g, 0.57 mmol), CsF (0.172 g, 1.1 mmol), PdCl$_2$(dppf) (0.083 g, 0.2 mmol). The crude was purified by reverse phase chromatography (C18, HCOOH/ACN). The resulting formate salt was dissolved in H$_2$O, washed with AcOEt and the aqueous layer was basified with aqueous 10% NaHCO$_3$ solution. The precipitate was filtered off, washed with H$_2$O and with Et$_2$O to give 0.080 g of the title product. Yield=26%. HPLC-MS (ESI) m/z: 415.12 [M-H]$^+$. $^1$H NMR (300 MHz, DMSO-d$_6$): δ 13.74 (s, 1H), 8.84 (d, J=2.3 Hz, 1H), 8.74 (t, J=6.1 Hz, 1H), 8.53 (d, J=1.9 Hz, 1H), 8.44 (s, 1H), 8.02 (t, J=2.2 Hz, 1H), 7.78 (qd, J=8.8, 1.3 Hz, 2H), 4.56 (s, 2H), 3.49-3.41 (m, 2H), 3.37 (s, 3H), 3.24-3.15 (m, 2H), 3.13-3.01 (m, 1H), 2.92 (dd, J=13.2, 9.2 Hz, 1H), 2.80-2.68 (m, 1H), 2.29-2.18 (m, 1H), 1.98-1.79 (m, 1H).

5-(5-(Hydroxymethyl)pyridin-3-yl)-N-(1,1-dioxidotetrahydrothiophen-3-yl)-1H-indazole-3-carboxamide (Example 6). The title compound was obtained according to general procedure C, step 1, method (A) using N-(1,1-dioxo-1λ$^6$-thiolan-3-yl)-5-(4,4,5,5-tetramethyl-1,3,2-dioxaborolan-2-yl)-1H-indazole-3-carboxamide (Vb, 0.23 g, 0.6 mmol), (5-bromopyridin-3-yl)methanol (VIIa, 0.12 g, 0.60 mmol), CsF (0.172 g, 1.1 mmol), PdCl$_2$(dppf) (0.083 g, 0.2 mmol). The crude was purified by reverse phase chromatography (C18, HCOOH/ACN). The resulting formate salt was dissolved in H$_2$O, washed with AcOEt and the aqueous layer was basified with aqueous 10% NaHCO$_3$ solution. The precipitate was filtered off, washed with H$_2$O and with Et$_2$O to give 0.060 g of the title product. Yield=26%. HPLC-MS (ESI) m/z: 387.1 [M-H]$^+$. $^1$H NMR (300 MHz, DMSO-d$_6$): δ 13.83 (s, 1H), 8.90 (d, J=7.8 Hz, 1H), 8.80 (d, J=2.3 Hz, 1H), 8.53 (d, J=1.9 Hz, 1H), 8.44 (s, 1H), 8.03 (d, J=2.3 Hz, 1H), 7.79 (d, J=3.0 Hz, 2H), 5.43 (d, J=6.3 Hz, 1H), 4.79 (p, J=7.7 Hz, 1H), 4.65 (d, J=4.6 Hz, 2H), 3.57-3.40 (m, 2H), 3.28-3.15 (m, 2H), 2.39-2.24 (m, 2H).

5-(2,3-Difluorophenyl)-N-((tetrahydro-2H-pyran-4-yl)methyl)-1H-indazole-3-carboxamide (Example 7). The title compound was obtained according to general procedure C, step 1, method (B) using 5-bromo-N-((tetrahydro-2H-pyran-4-yl)methyl)-1H-indazole-3-carboxamide (IVa, 0.107 g, 0.316 mmol), 2,3-difluorophenylboronic acid (XIIb, 0.200 g, 1.266 mmol), Cs$_2$CO$_3$ (0.412 g, 1.266 mmol), PdCl$_2$(dppf) (0.058 g, 0.079 mmol). The crude was purified by flash chromatography (SiO$_2$, Cyclohexane/EtOAc) to give 0.016 g of the title product. Yield=14%. HPLC-MS (ESI) m/z: 372.1 [M-H]$^+$. $^1$H NMR (400 MHz, DMSO-d6): δ 13.69 (br. s., 1H), 8.45-8.48 (m, 1H), 8.33 (br. s., 1H), 7.70-7.73 (m, 1H), 7.58-7.61 (m, 1H), 7.36-7.47 (m, 2H), 7.28-7.33 (m, 1H), 3.80-3.84 (2H, m), 3.17-3.26 (m, 4H), 1.79-1.88 (m, 1H), 1.56-1.59 (m, 2H), 1.14-1.24 (m, 2H).

5-(2,3-Difluorophenyl)-N-(1,1-dioxidotetrahydrothiophen-3-yl)-1H-indazole-3-carboxamide (Example 10). The title compound was obtained according to general procedure C, step 1, method (B) using 5-bromo-N-(1,1-dioxidotetrahydrothiophen-3-yl)-1H-indazole-3-carboxamide (IVb, 0.22 g, 0.614 mmol), 2,3-difluorophenylboronic acid (XIIb, 0.194 g, 1.228 mmol), Cs$_2$CO$_3$ (0.400 g, 1.228 mmol), PdCl$_2$(dppf) (0.045 g, 0.061 mmol). The crude was purified by flash chromatography (SiO$_2$, Cyclohexane/EtOAc) to give 0.072 g of the title product. Yield=28.5%. HPLC-MS (ESI) m/z: 392.0 [M-H]$^+$. $^1$H NMR (400 MHz, DMSO-d6): δ 13.83 (br. s., 1H), 8.86-8.88 (m, 1H), 8.33 (br. s., 1H), 7.73-7.76 (m, 1H), 7.60-7.63 (m, 1H), 7.28-7.47 (m, 3H), 4.73-4.82 (m, 1H), 3.44-3.52 (m, 1H), 3.34-3.40 (m, 1H), 3.16-3.23 (m, 2H), 2.38-2.44 (m, 1H), 2.26-2.33 (m, 1H).

5-(5-Isopropoxypyridin-3-yl)-N-(1,1-dioxidotetrahydrothiophen-3-yl)methyl)-1H-indazole-3-carboxamide (Example 11). The title compound was obtained according to general procedure C, step 1, method (A) using 5-bromo-N-[(1,1-dioxo-1λ$^6$-thiolan-3-yl)methyl]-1H-indazole-3-carboxamide (IVh, 0.200 g, 0.50 mmol), (5-isopropoxypyridin-3-yl)boronic acid (XIIa, 0.170 g, 0.60 mmol), CsF (0.163 g, 1.1 mmol), PdCl$_2$(dppf) (0.094 g, 0.1 mmol). The crude was purified by flash chromatography (SiO$_2$, DCM/MeOH) to give 0.1 g of the title product. Yield=48%. HPLC-MS (ESI) m/z: 429.4 [M-H]$^+$. $^1$H NMR (300 MHz, DMSO-d$_6$): δ 13.75 (s, 1H), 8.75 (t, J=6.1 Hz, 1H), 8.44 (dd, J=12.4, 1.6 Hz, 2H), 8.27 (d, J=2.7 Hz, 1H), 7.86-7.69 (m, 2H), 7.66-7.52 (m, 1H), 4.87 (p, J=6.1 Hz, 1H), 3.46 (td, J=6.5, 2.1 Hz, 2H), 3.29-3.17 (m, 2H), 3.15-3.01 (m, 1H), 2.93 (dd, J=13.2, 9.3 Hz, 1H), 2.83-2.67 (m, 1H), 2.31-2.16 (m, 1H), 1.99-1.80 (m, 1H), 1.34 (d, J=6.0 Hz, 6H).

5-(2,3-Difluorophenyl)-N-((tetrahydrofuran-2-yl)methyl)-1H-indazole-3-carboxamide (Example 13). The title compound was obtained according to general procedure C, step 1, method (B) using 5-bromo-N-((tetrahydrofuran-2-yl)methyl)-1H-indazole-3-carboxamide (IVc, 0.158 g, 0.487 mmol), 2,3-difluorophenylboronic acid (XIIb, 0.154 g, 0.975 mmol), Cs$_2$CO$_3$ (0.318 g, 0.975 mmol), PdCl$_2$(dppf) (0.036 g, 0.049 mmol). The crude was purified by flash chromatography (SiO$_2$, Cyclohexane/EtOAc) to give 0.060 g of the title product. Yield=31%. HPLC-MS (ESI) m/z: 358.1 [M-H]$^+$. $^1$H NMR (400 MHz, DMSO-d6): δ 13.72 (br. s., 1H), 8.33 (br. s., 1H), 8.25-8.28 (m, 1H), 7.71-7.74 (m, 1H), 7.58-7.61 (m, 1H), 7.36-7.47 (m, 2H), 7.28-7.33 (m, 1H), 3.98-4.04 (m, 1H), 3.74-3.80 (m, 1H), 3.59-3.64 (m, 1H), 3.33-3.36 (m, 2H), 1.75-1.93 (m, 3H), 1.58-1.66 (m, 1H).

5-(2,3-Difluorophenyl)-N-((tetrahydro-2H-pyran-2-yl)methyl)-1H-indazole-3-carboxamide (Example 14). The title compound was obtained according to general procedure C, step 1, method (B) using 5-bromo-N-((tetrahydro-2H-pyran-2-yl)methyl)-1H-indazole-3-carboxamide (IVd, 0.141 g, 0.417 mmol), 2,3-difluorophenylboronic acid (XIIb, 0.132 g, 0.834 mmol), Cs$_2$CO$_3$ (0.27 g, 0.834 mmol), PdCl$_2$(dppf) (0.031 g, 0.042 mmol). The crude was purified by flash chromatography (SiO$_2$, Cyclohexane/EtOAc) to give 0.019 g of the title product. Yield=12%. HPLC-MS (ESI) m/z: 372.1 [M-H]$^+$. $^1$H NMR (400 MHz, DMSO-d6): δ 8.35 (br. s., 1H), 8.18-8.21 (m, 1H), 7.73-7.75 (m, 1H), 7.60-7.63 (m, 1H), 7.36-7.48 (m, 2H), 7.30-7.35 (m, 1H), 3.87-3.90 (m, 1H), 3.45-3.51 (m, 2H), 3.27-3.30 (m, 2H), 1.74-1.81 (m, 1H), 1.61-1.64 (m, 1H), 1.42-1.48 (m, 3H), 1.16-1.25 (m, 1H).

5-(2,3-Difluorophenyl)-N-((tetrahydrofuran-3-yl)methyl)-1H-indazole-3-carboxamide (Example 15). The title compound was obtained according to general procedure C, step 1, method (B) using 5-bromo-N-((tetrahydrofuran-3-yl)methyl)-1H-indazole-3-carboxamide (IVe, 0.269 g, 0.830 mmol), 2,3-difluorophenylboronic acid (XIIb, 0.262 g, 1.660 mmol), $Cs_2CO_3$ (0.541 g, 1.660 mmol), $PdCl_2$(dppf) (0.061 g, 0.083 mmol). The crude was purified by flash chromatography ($SiO_2$, Cyclohexane/EtOAc) to give 0.015 g of the title product. Yield=5%. HPLC-MS (ESI) m/z: 358.1 [M-H]$^+$. $^1$H NMR (400 MHz, DMSO-d6): δ 13.72 (br. s., 1H), 8.59-8.62 (m, 1H), 8.33 (br. s., 1H), 7.71-7.73 (m, 1H), 7.59-7.61 (m, 1H), 7.28-7.47 (m, 3H), 3.57-3.76 (m, 3H), 3.47-3.51 (m, 1H), 3.26-3.31 (m, 2H), 2.52-2.56 (m, 1H), 1.87-1.95 (m, 1H), 1.58-1.66 (m, 1H). The racemic mixture was then separated by chiral chromatography to give the two final enantiomers 5-(2,3-difluorophenyl)-N—(((S)-tetrahydrofuran-3-yl)methyl)-1H-indazole-3-carboxamide (Example 8) and 5-(2,3-Difluorophenyl)-N—(((R)-tetrahydrofuran-3-yl)methyl)-1H-indazole-3-carboxamide (Example 9).

5-(5-((Dimethylamino)methyl)pyridin-3-yl)-N-((tetrahydro-2H-pyran-4-yl)methyl)-1H-indazole-3-carboxamide (Example 16). The title compound was obtained according to general procedure C, step 1, method (A) using N-((tetrahydro-2H-pyran-4-yl)methyl)-5-(4,4,5,5-tetramethyl-1,3,2-dioxaborolan-2-yl)-1H-indazole-3-carboxamide (Va, 0.1 g, 0.26 mmol), 1-(5-bromopyridin-3-yl)-N,N-dimethylmethanamine (Xa, 0.11 g, 0.52 mmol), CsF (0.079 g, 0.52 mmol), $PdCl_2$(dppf) (0.019 g, 0.026 mmol). The crude was purified by flash chromatography ($SiO_2$, DCM/MeOH) to give 0.046 g of the title product. Yield=45%. HPLC-MS (ESI) m/z: 394.2 [M-H]$^+$. $^1$H NMR (400 MHz, $CD_3OD$): δ 8.78 (d, J=1.9 Hz, 1H), 8.53-8.48 (m, 1H), 8.14 (t, J=2.0 Hz, 1H), 7.77-7.68 (m, 2H), 3.95 (dd, J=11.5, 2.6 Hz, 2H), 3.63 (s, 2H), 3.40 (td, J=11.9, 2.1 Hz, 2H), 3.36-3.33 (m, 2H), 2.45 (s, 6H), 1.98-1.87 (m, 1H), 1.75-1.69 (m, 2H), 1.43-1.32 (m, 2H).

5-(5-(Pyrrolidin-1-ylmethyl)pyridin-3-yl)-N-((tetrahydro-2H-pyran-4-yl)methyl)-1H-indazole-3-carboxamide (Example 17). The title compound was obtained according to general procedure C, step 1, method (A) using N-((tetrahydro-2H-pyran-4-yl)methyl)-5-(4,4,5,5-tetramethyl-1,3,2-dioxaborolan-2-yl)-1H-indazole-3-carboxamide (Va, 0.1 g, 0.26 mmol), 3-bromo-5-[(pyrrolidin-1-yl)methyl]pyridine (Xb, 0.13 g, 0.52 mmol), CsF (0.079 g, 0.52 mmol), $PdCl_2$(dppf) (0.019 g, 0.026 mmol). The crude was purified by flash chromatography ($SiO_2$, DCM/MeOH) to give 0.068 g of the title product. Yield=62%. HPLC-MS (ESI) m/z: 420.2 [M-H]$^+$. $^1$H NMR (400 MHz, $CD_3OD$): δ 8.80 (d, J=2.2 Hz, 1H), 8.55-8.49 (m, 2H), 8.15 (t, J=2.1 Hz, 1H), 7.78-7.67 (m, 2H), 3.95 (dd, J=11.5, 2.7 Hz, 2H), 3.84 (s, 2H), 3.47-3.37 (m, 2H), 3.37-3.34 (m, 2H), 2.74-2.65 (m, 4H), 1.97-1.89 (m, 1H), 1.89-1.82 (m, 4H), 1.76-1.67 (m, 2H), 1.44-1.31 (m, 2H).

5-(4-(Hydroxymethyl)pyridin-3-yl)-N-((tetrahydro-2H-pyran-4-yl)methyl)-1H-indazole-3-carboxamide (Example 18). The title compound was obtained according to general procedure C, step 1, method (C) using N-((tetrahydro-2H-pyran-4-yl)methyl)-5-(4,4,5,5-tetramethyl-1,3,2-dioxaborolan-2-yl)-1H-indazole-3-carboxamide (Va, 0.1 g, 0.26 mmol), 3-bromopyridine-4-carbaldehyde (VIb, 0.053 g, 0.29 mmol), $Na_2CO_3$ (0.055 g, 0.52 mmol), Pd(PPh$_3$)$_4$ (0.015 g, 0.013 mmol). The crude was purified by flash chromatography ($SiO_2$, DCM/MeOH) to give 0.013 g of the title product. Yield=14%. HPLC-MS (ESI) m/z: 367.1 [M-H]$^+$. $^1$H NMR (400 MHz, $CD_3OD$): δ 8.53 (d, J=5.2 Hz, 1H), 8.40 (bs, 1H), 8.19-8.16 (m, 1H), 7.69 (dd, J=15.8, 6.9 Hz, 2H), 7.41 (dd, J=8.6, 1.6 Hz, 1H), 4.61 (s, 2H), 3.94 (dd, J=11.4, 2.8 Hz, 2H), 3.39 (td, J=11.8, 2.0 Hz, 2H), 3.32 (d, J=7.0 Hz, 2H), 1.99-1.85 (m, 1H), 1.75-1.65 (m, 2H), 1.42-1.24 (m, 2H).

5-(4-(Pyrrolidin-1-ylmethyl)pyridin-3-yl)-N-((tetrahydro-2H-pyran-4-yl)methyl)-1H-indazole-3-carboxamide (Example 19). The title compound was obtained according to general procedure C, step 1, method (A) using N-((tetrahydro-2H-pyran-4-yl)methyl)-5-(4,4,5,5-tetramethyl-1,3,2-dioxaborolan-2-yl)-1H-indazole-3-carboxamide (Va, 0.1 g, 0.26 mmol), 3-bromo-4-(pyrrolidin-1-ylmethyl)pyridine (Xc, 0.094 g, 0.39 mmol), CsF (0.079 g, 0.52 mmol), $PdCl_2$(dppf) (0.011 g, 0.013 mmol). The crude was purified by reverse phase chromatography (C18, $NH_4HCO_3$/ACN) to give 0.009 g of the title product. Yield=8%. HPLC-MS (ESI) m/z: 420.2 [M-H]$^+$. $^1$H NMR (400 MHz, $CD_3OD$): δ 8.51 (d, J=5.1 Hz, 1H), 8.44 (s, 1H), 8.24-8.21 (m, 1H), 7.70-7.66 (m, 2H), 7.44 (dd, J=8.6, 1.6 Hz, 1H), 3.98-3.92 (m, 2H), 3.67 (s, 2H), 3.40 (td, J=11.9, 2.1 Hz, 2H), 3.35-3.32 (m, 2H), 2.49-2.37 (m, 4H), 1.98-1.87 (m, 1H), 1.77-1.67 (m, 6H), 1.44-1.30 (m, 2H).

5-(4-(Morpholinomethyl)pyridin-3-yl)-N-((tetrahydro-2H-pyran-4-yl)methyl)-1H-indazole-3-carboxamide carboxamide (Example 20). The title compound was obtained according to general procedure C, step 1, method (A) using N-((tetrahydro-2H-pyran-4-yl)methyl)-5-(4,4,5,5-tetramethyl-1,3,2-dioxaborolan-2-yl)-1H-indazole-3-carboxamide (Va, 0.1 g, 0.26 mmol), 4-[(3-bromopyridin-4-yl)methyl]morpholine (Xd, 0.094 g, 0.39 mmol), CsF (0.079 g, 0.52 mmol), $PdCl_2$(dppf) (0.011 g, 0.013 mmol). The crude was purified by reverse phase chromatography (C18, $NH_4HCO_3$/ACN) to give 0.030 g of the title product. Yield=26%. HPLC-MS (ESI) m/z: 436.2 [M-H]$^+$. $^1$H NMR (400 MHz, $CD_3OD$): δ 8.50 (d, J=5.2 Hz, 1H), 8.45 (s, 1H), 8.27-8.25 (m, 1H), 7.69-7.66 (m, 2H), 7.45 (dd, J=8.6, 1.6 Hz, 1H), 3.98-3.93 (m, 2H), 3.65-3.61 (m, 4H), 3.50 (s, 2H), 3.41 (td, J=11.8, 2.0 Hz, 2H), 3.35-3.33 (m, 2H), 2.38-2.31 (m, 4H), 1.99-1.87 (m, 1H), 1.76-1.68 (m, 2H), 1.43-1.31 (m, 2H).

5-(4-((Dimethylamino)methyl)pyridin-3-yl)-N-((tetrahydro-2H-pyran-4-yl)methyl)-1H-indazole-3-carboxamide (Example 21). The title compound was obtained according to general procedure C, step 1, method (B) using N-((tetrahydro-2H-pyran-4-yl)methyl)-5-(4,4,5,5-tetramethyl-1,3,2-dioxaborolan-2-yl)-1H-indazole-3-carboxamide (Va, 0.12 g, 0.25 mmol), 1-(3-bromopyridin-4-yl)-N,N-dimethylmethanamine (Xe, 0.064 g, 0.30 mmol), $Cs_2CO_3$ (0.16 g, 0.50 mmol), $PdCl_2$(dppf) (0.019 g, 0.026 mmol). The crude was purified by reverse phase chromatography (C18, $NH_4HCO_3$/ACN) to give 0.013 g of the title product. Yield=13%. HPLC-MS (ESI) m/z: 394.2 [M-H]$^+$. $^1$H NMR (400 MHz, $CD_3OD$): δ 8.51 (d, J=5.2 Hz, 1H), 8.44 (s, 1H), 8.19 (s, 1H), 7.66 (t, J=7.3 Hz, 2H), 7.41 (dd, J=8.6, 1.5 Hz, 1H), 3.97-3.91 (m, 2H), 3.40 (td, J=11.8, 1.8 Hz, 2H), 3.33 (d, J=6.9 Hz, 2H), 2.13 (s, 6H), 1.98-1.86 (m, 1H), 1.74-1.67 (m, 2H), 1.42-1.29 (m, 2H).

5-(4-(Methoxymethyl)pyridin-3-yl)-N-((tetrahydro-2H-pyran-4-yl)methyl)-1H-indazole-3-carboxamide (Example 22). The title compound was obtained according to general procedure C, step 1, method (A) using N-((tetrahydro-2H-pyran-4-yl)methyl)-5-(4,4,5,5-tetramethyl-1,3,2-dioxaborolan-2-yl)-1H-indazole-3-carboxamide (Va, 0.2 g, 0.29 mmol), 3-bromo-4-(methoxymethyl)pyridine (VIIIb, 0.079 g, 0.39 mmol), CsF (0.079 g, 0.52 mmol), $PdCl_2$(dppf) (0.021 g, 0.026 mmol). The crude was purified by column reverse phase C18 ($NH_4HCO_3$/ACN) to give 0.046 g of the title product. Yield=6%. HPLC-MS (ESI) m/z: 381.1 [M-H]$^+$. $^1$H NMR (400 MHz, $CD_3OD$): δ 8.54 (d, J=5.2 Hz, 1H), 8.46 (s, 1H), 8.23-8.21 (m, 1H), 7.69 (dd, J=8.6, 0.8 Hz, 1H), 7.65-7.62 (m, 1H), 7.43 (dd, J=8.6, 1.7 Hz, 1H), 4.45 (s, 2H), 3.98-3.93 (m, 2H), 3.41 (td, J=11.9, 2.1 Hz, 2H), 3.35 (s, 3H), 3.34 (d, J=7.0 Hz, 2H), 1.98-1.87 (m, 1H), 1.75-1.68 (m, 2H), 1.43-1.31 (m, 2H).

5-(Pyridin-3-yl)-N-((tetrahydro-2H-pyran-4-yl)methyl)-1H-indazole-3-carboxamide (Example 23). The title compound was obtained according to general procedure C, step 1, method (A) using 5-bromo-N-((tetrahydro-2H-pyran-4-yl)methyl)-1H-indazole-3-carboxamide (IVa, 0.150 g, 0.44 mmol), 3-pyridylboronic acid (XIIc, 0.11 g, 0.89 mmol), CsF (0.13 g, 0.89 mmol), PdCl$_2$(dppf) (0.033 g, 0.044 mmol). The crude was purified by flash chromatography (SiO$_2$, DCM/MeOH) to give 0.053 g of the title product. Yield=35%. HPLC-MS (ESI) m/z: 337.2 [M-H]$^+$. $^1$H NMR (400 MHz, CD$_3$OD): δ 8.87 (d, J=1.8 Hz, 1H), 8.53-8.49 (m, 2H), 8.19-8.15 (m, 1H), 7.76-7.70 (m, 2H), 7.54 (dd, J=7.9, 4.9 Hz, 1H), 4.00-3.93 (m, 2H), 3.46-3.37 (m, 2H), 3.36 (d, J=6.9 Hz, 2H), 2.01-1.88 (m, 1H), 1.76-1.68 (m, 2H), 1.45-1.32 (m, 2H).

5-(4-(piperazin-1-ylmethyl)pyridin-3-yl)-N-((tetrahydro-2H-pyran-4-yl)methyl)-1H-indazole-3-carboxamide (Example 24). The title compound was obtained according to general procedure C, step 1, method (A) using 5-bromo-N-((tetrahydro-2H-pyran-4-yl)methyl)-1H-indazole-3-carboxamide (IVa, 0.1 g, 0.30 mmol), tert-butyl 4-{[3-(4,4,5,5-tetramethyl-1,3,2-dioxaborolan-2-yl)pyridin-4-yl]methyl}piperazine-1-carboxylate (XIa, 0.238 g, 0.59 mmol), CsF (0.090 g, 0.59 mmol), PdCl$_2$(dppf) (0.048 g, 0.06 mmol). The crude was purified by flash chromatography (SiO$_2$, CHCl$_3$/MeOH) to give 0.057 g of tert-butyl 5-(4-(piperazin-1-ylmethyl)pyridin-3-yl)-N-((tetrahydro-2H-pyran-4-yl)methyl)-1H-indazole-3-carboxamide. Yield=19%. The intermediate (0.13 g, 0.25 mmol) was then N-deprotected using 2N HCl solution in Et$_2$O (1.88 mL, 3.76 mmol). The crude was eluted through an SCX cartridge (5 g) to give 0.100 g of the title product. Yield: 87%. HPLC-MS (ESI) m/z: 435.1 [M-H]$^+$. $^1$H NMR (400 MHz, CD$_3$OD): δ 8.53 (d, J=5.1 Hz, 1H), 8.49 (s, 1H), 8.37 (bs, 1H), 7.70 (d, J=8.6 Hz, 1H), 7.64 (d, J=5.1 Hz, 1H), 7.43 (dd, J=8.6, 1.6 Hz, 1H), 4.00-3.93 (m, 2H), 3.58 (s, 2H), 3.46-3.38 (m, 2H), 3.34 (d, J=6.9 Hz, 2H), 3.18-3.13 (m, 2H), 2.63-2.51 (m, 4H), 1.98-1.88 (m, 1H), 1.76-1.68 (m, 2H), 1.44-1.30 (m, 2H).

5-(2,3-difluorophenyl)-N-(tetrahydrofuran-3-yl)-1H-indazole-3-carboxamide (Example 25). The title compound was obtained according to general procedure C, step 1, method (B) using 5-bromo-N-(tetrahydrofuran-3-yl)-1H-indazole-3-carboxamide (IVf, 0.169 g, 0.545 mmol), 2,3-difluorophenylboronic acid (XIIb, 0.172 g, 1.090 mmol), Cs$_2$CO$_3$ (0.35 g, 1.09 mmol), PdCl$_2$(dppf) (0.04 g, 0.054 mmol). The crude was purified by flash chromatography (SiO$_2$, DCM/MeOH) to give 0.027 g of the title product. Yield=10%. HPLC-MS (ESI) m/z: 344.2 [M-H]$^+$. $^1$H NMR (400 MHz, CDCl$_3$/CD$_3$OD): δ 8.53 (br. s., 1H), 7.54-7.66 (m, 3H), 7.13-7.18 (m, 2H), 4.75-4.83 (m, 1H), 3.83-4.07 (m, 5H), 2.34-2.44 (m, 1H).

5-(5-(morpholinomethyl)pyridin-3-yl)-N-((tetrahydro-2H-pyran-4-yl)methyl)-1H-indazole-3-carboxamide (Example 27). The title compound was obtained according to general procedure C, step 1, method (A) using 5-bromo-N-((tetrahydro-2H-pyran-4-yl)methyl)-1H-indazole-3-carboxamide (IVa, 0.1 g, 0.30 mmol), 4-((5-(4,4,5,5-tetramethyl-1,3,2-dioxaborolan-2-yl)pyridin-3-yl)methyl)morpholine (XIb, 0.400 g, 0.591 mmol), CsF (0.090 g, 0.59 mmol), PdCl$_2$(dppf) (0.048 g, 0.06 mmol). The crude was purified by reverse phase chromatography (C18, NH$_4$HCO$_3$/ACN) to give 0.024 g of the title product. Yield=17%. HPLC-MS (ESI) m/z: 436.2 [M-H]$^+$. $^1$H NMR (400 MHz, CD$_3$OD): δ 8.79 (d, J=2.2 Hz, 1H), 8.54-8.48 (m, 2H), 8.16 (t, J=2.1 Hz, 1H), 7.78-7.70 (m, 2H), 4.00-3.94 (m, 2H), 3.74-3.70 (m, 4H), 3.67 (s, 2H), 3.47-3.39 (m, 2H), 3.36 (d, J=7.0 Hz, 2H), 2.59-2.49 (m, 2H), 2.01-1.88 (m, 4H), 1.79-1.68 (m, 2H), 1.45-1.33 (m, 2H).

5-(5-((methylamino)methyl)pyridin-3-yl)-N-((tetrahydro-2H-pyran-4-yl)methyl)-1H-indazole-3-carboxamide (Example 28). The title compound was obtained according to general procedure C, step 1, method (A) using N-((tetrahydro-2H-pyran-4-yl)methyl)-5-(4,4,5,5-tetramethyl-1,3,2-dioxaborolan-2-yl)-1H-indazole-3-carboxamide (Va, 0.1 g, 0.26 mmol), 1-(5-bromopyridin-3-yl)-N-methylmethanamine (Xh, 0.078 g, 0.389 mmol), CsF (0.079 g, 0.519 mmol), PdCl$_2$(dppf) (0.011 g, 0.013 mmol). The crude was purified by reverse phase chromatography (C18, NH$_4$HCO$_3$/ACN) to give 0.020 g of the title product. Yield=19%. HPLC-MS (ESI) m/z: 380.1 [M-H]$^+$. $^1$H NMR (400 MHz, CD$_3$OD): δ 8.78 (d, J=1.9 Hz, 1H), 8.53-8.48 (m, 2H), 8.14 (t, J=2.0 Hz, 1H), 7.77-7.68 (m, 2H), 3.95 (dd, J=11.5, 2.6 Hz, 2H), 3.40 (td, J=11.9, 2.1 Hz, 2H), 3.36-3.33 (m, 2H), 2.45 (s, 3H), 1.98-1.87 (m, 1H), 1.75-1.69 (m, 2H), 1.43-1.32 (m, 2H).

General Procedure D: Synthesis of Compounds I (Example 12)

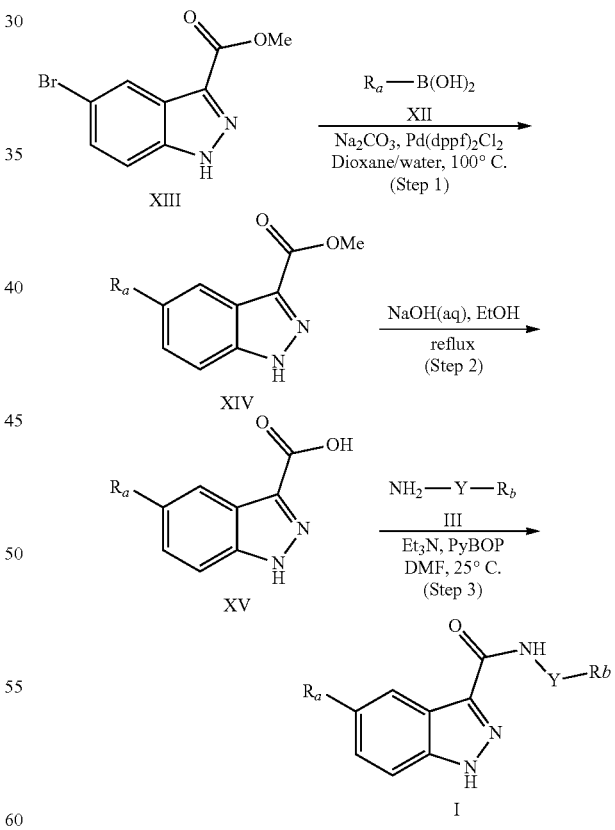

Step 1

To a mixture of methyl 5-bromo-1H-indazole-3-carboxylate (XIII, 1 eq.) and the proper boronic acid (XII, 2.5 eq.) in 1,4-dioxane, a solution of Na$_2$CO$_3$ (2 eq.) in water was added. The reaction mixture was degassed for 10 minutes and PdCl$_2$(dppf) (0.05 eq.; 1:1 complex with dichloromethane) was added. The reaction mixture was heated at 100° C. for 3 hours under Ar stream, cooled, diluted with water and extracted with EtOAc. The organic layer was washed with brine, dried and filtered. Removal of the solvent gave a residue that was purified by column chromatography to give intermediate having general formula XIV.

Methyl 5-(2,3-difluorophenyl)-1H-indazole-3-carboxylate (XIVa). The title compound was obtained according to general procedure D, step 1 using methyl 5-bromo-1H-indazole-3-carboxylate (XIII, 1.00 g, 3.92 mmol), (2,3-difluorophenyl)boronic acid (XIIb, 1.55 g, 9.81 mmol), Na$_2$CO$_3$ (0.83 g, 7.83 mmol), PdCl$_2$(dppf) (0.17 g, 0.21 mmol). The crude was purified by column chromatography (SiO$_2$, acetone/n-hexane) to give 0.60 g of the title product. Yield=53%.

Step 2

A mixture of carboxylate (XIV, 1 eq.) and aqueous 3N NaOH solution in EtOH (1:1) was heated at reflux for 3 hours. After cooling, the reaction mixture was made acid with aqueous 1N HCl solution (pH≈3) and extracted with EtOAc. The organic layer was washed with brine, dried and filtered. Evaporation of the solvent gave a residue that was purified by flash chromatography to give intermediate having general formula XV.

5-(2,3-Difluorophenyl)-1H-indazole-3-carboxylic acid (XVa). The title compound was obtained according to general procedure D, step 2 using methyl 5-(2,3-difluorophenyl)-1H-indazole-3-carboxylate (XIVa, 0.60 g, 2.08 mmol), aqueous 3N NaOH solution (8 mL) in EtOH (8 mL). The crude was purified by flash chromatography (SiO$_2$, CHCl$_3$/MeOH) to give 0.55 g of the title product. Yield=96%.

Step 3

A mixture of acid (XV, 1 eq.), the proper amine (III, 1.5 eq.), Et$_3$N (1.5 eq.) and PyBOP (1 eq.) in anhydrous DMF was stirred at 25° C. for 12 hours, diluted with water and extracted with EtOAc. The organic layer was washed with brine, dried and filtered. Evaporation of the solvent gave a residue that was purified by flash chromatography to give the final compound with general formula I.

5-(2,3-difluorophenyl)-N-((tetrahydro-2H-pyran-3-yl)methyl)-1H-indazole-3-carboxamide (Example 12). The title compound was obtained according to general procedure D, step 3 using 5-(2,3-difluorophenyl)-1H-indazole-3-carboxylic acid (XVa, 0.07 g, 0.25 mmol), (tetrahydro-2H-pyran-3-yl)methanamine (IIIh, 0.04 g, 0.37 mmol), Et$_3$N (0.04 g, 0.05 mL, 0.37 mmol) and PyBOP (0.13 g, 0.25 mmol). The crude was purified by flash chromatography (SiO$_2$, CHCl$_3$/MeOH, then C18, H$_2$O/ACN/0.01% TFA) to give 0.02 g of the title product. Yield=18%. HPLC-MS (ESI) m/z: 372.1 [M-H]$^+$. $^1$H NMR (400 MHz, DMSO-d6): δ 1.20-1.29 (m, 1H), 1.39-1.49 (m, 1H), 1.56-1.60 (m, 1H), 1.75-1.79 (m, 1H), 1.82-1.90 (m, 1H), 3.10-3.24 (m, 3H), 3.27-3.30 (m, 1H), 3.68-3.71 (m, 1H), 3.77 (dd, J=2.9 and 11.2 Hz, 1H), 7.28-7.33 (m, 1H), 7.37-7.47 (m, 2H), 7.59-7.61 (m, 1H), 7.72-7.74 (m, 1H), 8.34 (s, 1H), 8.50 (t, J=6.1 Hz, 1H), 13.67 ppm (br s, 1H).

Pharmacological Properties

The pharmacological properties of the compounds of formula (I) useful in the present invention were evaluated by the methods described in the following sections.

The compounds of the invention were assessed together with comparison compound C having the structure reported below (corresponding to compound 8 of WO2013124158).

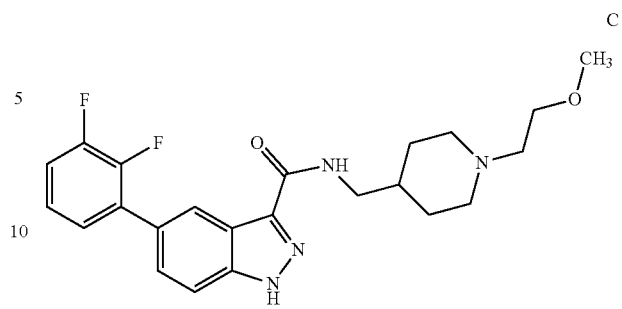

Test I—Activity on Human GSK-3β (Test In Vitro)

The activity on human GSK-3β of the compounds of the invention listed in the following Table 1 and of the comparison compound C was assessed at five concentrations ranging from 10 μM to 1 nM with ten-fold dilutions in duplicate using the following methods (according to Meijer et al., Chem. Biol., 2003-10:1255-1266).

Human recombinant enzyme GSK-3β was incubated for 90 minutes at 22° C. in the presence of compounds or vehicle in a reaction buffer containing ATP plus 100 nM unphosphorylated specific substrate peptide (Ulight-CFFKNIVTPRTPPPSQGK-amide). Substrate phosphorylation was measured by LANCE technology (PerkinElmer, CT, USA).

The IC$_{50}$ values (concentration causing a half maximal inhibition of control specific activity) were determined by non-linear regression analysis of the inhibition curves generated with mean replicate values using Hill equation curve fitting.

Test II—Selectivity on hERG Channel (Test In Vitro)

Confirmation of interaction with the potassium channels of the compounds of the invention listed in the following Table 1 and of the comparison compound C was made by means of the automated whole-cell patch clamp test described in Mathes, C. (2006), Expert Opin. Ther. Targets, 10 (2): 230-241 using the recombinant human cell line CHO-K1, which stably expresses the hERG ion channel.

The IC$_{50}$ values (concentration causing a half maximal inhibition of control specific activity) were determined at five concentrations ranging from 100 μM to 10 nM with ten-fold dilutions in duplicate.

The degree of inhibition (%) was obtained by measuring the tail current amplitude, which is induced by a one second test pulse to −40 mV after a two second pulse to +20 mV, before and after drug incubation (the difference current was normalized to control and multiplied by 100 to obtain the percent of inhibition). Concentration (log) response curves were fitted to a logistic equation (three parameters assuming complete block of the current at very high test compound concentrations) to generate estimates of the 50% inhibitory concentration (IC50). The concentration response relationship of each compound was constructed from the percentage reductions of current amplitude by sequential concentrations.

Results of Test I and II

The results obtained are given in the following Table 1, together with the ratio between hERG and GSK-3β values.

TABLE 1

| Compound No | GSK-3β IC$_{50}$ [μM] | hERG IC$_{50}$ [μM] | hERG/GSK-3β Ratio |
|---|---|---|---|
| 1 | 0.0040 | 0.86 | 215 |
| 2 | 0.0060 | 5.7 | 950 |
| 3 | 0.0045 | 96 | 21,333 |
| 4 | 0.017 | 6.2 | 365 |
| 5 | 0.016 | >100 | — |
| 6 | 0.017 | >100 | — |
| 7 | 0.014 | 4 | 286 |
| 8 | 0.032 | 5.5 | 172 |
| 9 | 0.015 | 19 | 1,267 |
| 10 | 0.014 | 15 | 1,071 |
| 11 | 0.012 | 5.4 | 450 |
| 12 | 0.020 | 22 | 1,100 |
| 13 | 0.055 | 11 | 200 |
| 14 | 0.436 | >100 | — |
| 15 | 0.026 | 4.3 | 165 |
| 16 | 0.023 | 44 | 1,913 |
| 17 | 0.017 | 6.7 | 394 |
| 18 | 0.033 | 41 | 1,242 |
| 19 | 0.14 | 16 | 114 |
| 20 | 0.0185 | 46 | 2,487 |
| 21 | 0.22 | 40 | 182 |
| 22 | 0.028 | 47 | 1,679 |
| 23 | 0.022 | 49 | 2,227 |
| 24 | 0.12 | 93.8 | 782 |
| 25 | 0.13 | 13 | 100 |
| 27 | 0.013 | 3.5 | 269 |
| 28 | 0.0060 | >100 | — |
| C | 0.0216 | 0.0499 | 2.3 |

The invention claimed is:

1. A 1H-indazole-3-carboxamide compound having the following formula (I):

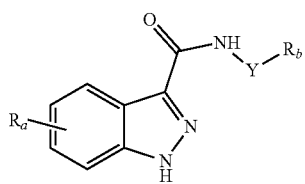

wherein $R_a$ is a carbocyclic or heterocyclic ring, aliphatic or aromatic, having from 3 to 12 members, optionally substituted by one or more substituents selected from the group consisting of halogen, hydroxy, $C_1$-$C_6$ alkyl, hydroxy $C_1$-$C_6$ alkyl, $C_1$-$C_6$ alkoxy, hydroxy $C_1$-$C_6$ alkoxy, $C_1$-$C_6$ alkoxy $C_1$-$C_6$ alkyl, $C_1$-$C_6$ alkoxy $C_1$-$C_6$ alkoxy and $C_1$-$C_6$ alkyl amino;

Y is a bond, a $C_1$-$C_6$ alkyl, $C_2$-$C_6$ alkenyl or $C_2$-$C_6$ alkynyl group, optionally substituted by one or more substituents selected from the group consisting of halogen, hydroxy, —NH$_2$, $C_1$-$C_3$ alkyl and $C_1$-$C_3$ alkoxy;

$R_b$ is a 1,1-dioxothiolanyl group, a thiolanyl group, an oxolanyl group, a thianyl group or an oxanyl group, optionally substituted by one or more substituents selected from the group consisting of halogen, hydroxy, —NH$_2$, oxo (═O), $C_1$-$C_3$ alkyl and $C_1$-$C_3$ alkoxy;

or an addition salt thereof with a pharmaceutically acceptable organic or inorganic acid or base, provided that:

when $R_b$ is an oxanyl group, Y is not a bond; and when $R_b$ is an oxolanyl group and $R_a$ is a pyridinyl or a monofluoropyridinyl group, Y is not a —CH$_2$— group.

2. The 1H-indazole-3-carboxamide compound according to claim 1, wherein $R_a$ is a carbocyclic or heterocyclic ring, aliphatic or aromatic, having from 4 to 10 members.

3. The 1H-indazole-3-carboxamide compound according to claim 1, wherein $R_a$ is a carbocyclic or heterocyclic ring, aliphatic or aromatic, having from 5 to 6 members.

4. The 1H-indazole-3-carboxamide compound according to claim 1, wherein $R_a$ is an aromatic carbocyclic or heterocyclic ring, having 6 members.

5. The 1H-indazole-3-carboxamide compound according to claim 1, wherein Y is a bond or a $C_1$-$C_6$ alkyl group.

6. The 1H-indazole-3-carboxamide compound according to claim 1, wherein said $C_1$-$C_6$ alkyl amino is a $C_1$-$C_6$ alkyl group wherein one or more hydrogen atom of the alkyl chain is substituted by an amino group having the formula —NR$_1$R$_2$, wherein R$_1$ and R$_2$ are independently a hydrogen atom, a $C_1$-$C_4$ alkyl group, a $C_2$-$C_4$ alkenyl group, a $C_2$-$C_4$ alkynyl group, and a phenyl group, or R$_1$ and R$_2$ together with the nitrogen atom form an aliphatic heterocyclic ring having 5 to 6 members, optionally comprising at least one additional heteroatom selected from nitrogen, sulfur, and oxygen.

7. The 1H-indazole-3-carboxamide compound according to claim 6, wherein said aliphatic heterocyclic ring formed by R$_1$ and R$_2$ together with the nitrogen atom of said —NR$_1$R$_2$ amino group is a pyrrolidine, oxazolidine, thiazolidine, piperidine, piperazine, morpholine, or thiomorpholine ring.

8. A method for the treatment of a disease arising from the uncontrolled activation and/or overexpression of GSK-3β, selected from the group consisting of (i) an insulin-resistance disorder; (ii) a neurodegenerative disease; (iii) a mood disorder; (iv) a schizophrenic disorder; (v) a cancerous disorder; (vi) inflammation, (vii) osteoporosis, (viii) cardiac hypertrophy, (ix) epilepsy, and (x) neuropathic pain, comprising administering to a subject in need thereof an effective amount of a 1H-indazole-3-carboxamide compound having the following formula (I):

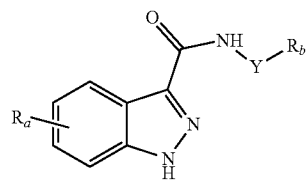

wherein $R_a$ is a carbocyclic or heterocyclic ring, aliphatic or aromatic, having from 3 to 12 members, optionally substituted by one or more substituents selected from the group consisting of halogen, hydroxy, $C_1$-$C_6$ alkyl, hydroxy $C_1$-$C_6$ alkyl, $C_1$-$C_6$ alkoxy, hydroxy $C_1$-$C_6$ alkoxy, $C_1$-$C_6$ alkoxy $C_1$-$C_6$ alkyl, $C_1$-$C_6$ alkoxy $C_1$-$C_6$ alkoxy and $C_1$-$C_6$ alkyl amino;

Y is a bond, a $C_1$-$C_6$ alkyl, $C_2$-$C_6$ alkenyl or $C_2$-$C_6$ alkynyl group, optionally substituted by one or more substituents selected from the group consisting of halogen, hydroxy, —NH$_2$, $C_1$-$C_3$ alkyl and $C_1$-$C_3$ alkoxy;

$R_b$ is a 1,1-dioxothiolanyl group, a thiolanyl group, an oxolanyl group, a thianyl group or an oxanyl group, optionally substituted by one or more substituents selected from the group consisting of halogen, hydroxy, —NH$_2$, oxo (═O), $C_1$-$C_3$ alkyl and $C_1$-$C_3$ alkoxy;

or an addition salt thereof with a pharmaceutically acceptable organic or inorganic acid or base.

9. The method according to claim 8, wherein said insulin-resistance disorder is selected from the group consisting of type-2 diabetes, syndrome X, obesity and polycystic ovary syndrome.

10. The method according to claim 8, wherein said neurodegenerative disease is selected from the group consisting of Parkinson's disease, Alzheimer's disease and Huntington's disease.

11. The method according to claim 8, wherein said mood disorder is selected from the group consisting of a bipolar disorder, and a depressive disorder.

12. The method according to claim 8, wherein said schizophrenic disorder is selected from the group consisting of paranoid schizophrenia, disorganized schizophrenia, catatonic schizophrenia, simple schizophrenia, residual schizophrenia, and undifferentiated schizophrenia.

13. The method according to claim 8, wherein said cancerous disorder is selected from the group consisting of prostate, pancreatic, ovarian, and colon-rectal cancer and MLL-associated leukaemia.

14. A pharmaceutical composition, comprising an effective amount of at least one compound of formula (I) as defined in claim 1, a salt thereof with a pharmaceutically acceptable organic or inorganic acid or base, and at least one inert pharmaceutically acceptable excipient.

15. The method according to claim 8, wherein said mood disorder is selected from the group consisting of bipolar I disorder, bipolar II disorder, cyclothymia, bipolar disorder not otherwise specified (BD-NOS), atypical depression (AD), melancholic depression, psychotic major depression (PMD), catatonic depression, postpartum depression (PPD), seasonal affective disorder (SAD), dysthymia, and depressive disorder not otherwise specified (DD-NOS).

16. The 1H-indazole-3-carboxamide compound according to claim 1, wherein $R_b$ is a 1,1-dioxothiolanyl group.

17. The 1H-indazole-3-carboxamide compound according to claim 1, wherein $R_b$ is a thiolanyl group.

18. The 1H-indazole-3-carboxamide compound according to claim 1, wherein $R_b$ is an oxolanyl group.

19. The 1H-indazole-3-carboxamide compound according to claim 1, wherein $R_b$ is a thianyl group.

20. The 1H-indazole-3-carboxamide compound according to claim 1, wherein $R_b$ is an oxanyl group.

\* \* \* \* \*